(12) United States Patent
Noda et al.

(10) Patent No.: US 10,278,873 B2
(45) Date of Patent: *May 7, 2019

(54) ABSORBENT ARTICLE HAVING A DOMED SECTION AND METHOD OF MANUFACTURING SAME

(71) Applicant: UNICHARM CORPORATION, Shikokuchuo-shi, Ehime (JP)

(72) Inventors: Yuki Noda, Kanonji (JP); Tatsuya Tamura, Kanonji (JP); Akira Hashino, Kanonji (JP)

(73) Assignee: UNICHARM CORPORATION, Ehime (JP)

( * ) Notice: Subject to any disclaimer, the term of this patent is extended or adjusted under 35 U.S.C. 154(b) by 88 days.

This patent is subject to a terminal disclaimer.

(21) Appl. No.: 14/368,521

(22) PCT Filed: Dec. 19, 2012

(86) PCT No.: PCT/JP2012/082977

§ 371 (c)(1),
(2) Date: Jun. 25, 2014

(87) PCT Pub. No.: WO2013/099739

PCT Pub. Date: Jul. 4, 2013

(65) Prior Publication Data

US 2015/0032073 A1    Jan. 29, 2015

(30) Foreign Application Priority Data

Dec. 28, 2011 (JP) .................................. 2011-289970

(51) Int. Cl.
*A61F 13/15* (2006.01)
*A61L 15/20* (2006.01)
(Continued)

(52) U.S. Cl.
CPC .. *A61F 13/47218* (2013.01); *A61F 13/15699* (2013.01); *A61F 13/4756* (2013.01);
(Continued)

(58) Field of Classification Search
USPC ............................................ 604/385.01, 367
See application file for complete search history.

(56) References Cited

U.S. PATENT DOCUMENTS

| 3,929,135 A | 12/1975 | Thompson |
| 4,588,630 A | 5/1986 | Shimalla |

(Continued)

FOREIGN PATENT DOCUMENTS

| CN | 1358484 A | 7/2002 |
| CN | 1432352 A | 7/2003 |

(Continued)

OTHER PUBLICATIONS

International Search Report dated Jul. 3, 2012 in corresponding International Application No. PCT/JP2012/058499.
(Continued)

*Primary Examiner* — Michele M Kidwell
(74) *Attorney, Agent, or Firm* — Hauptman Ham, LLP

(57) ABSTRACT

An objective of the present invention is to provide an absorbent article with which, both when dry, prior to absorbing blood, and when wet, after absorbing blood, is provided with a fit in a wearer's excretory orifice, especially the labia minora, and which is not prone to leaking. Provided is an absorbent article, including a liquid-permeable top sheet, a non liquid-permeable back sheet, and an absorbent body between the liquid-permeable top sheet and the non liquid-permeable back sheet. The absorbent article further comprises a center high part which protrudes in the thickness direction of the absorbent article in an excretory orifice contact region. The center high part further includes a (Continued)

portion of the top sheet, and a cushion part which is positioned between the top sheet and the absorbent body. The center high part further includes a central part, and an outer circumference part which surrounds the central part. The density of the cushion part in the outer circumference part is greater than the density of the cushion part in the central part.

20 Claims, 8 Drawing Sheets

(51) Int. Cl.
  *A61F 13/472* (2006.01)
  *A61F 13/475* (2006.01)
  *A61L 15/34* (2006.01)
  *A61L 15/44* (2006.01)
  *B32B 37/02* (2006.01)
  *B32B 37/10* (2006.01)
  *B32B 37/16* (2006.01)
(52) U.S. Cl.
  CPC .............. *A61L 15/20* (2013.01); *A61L 15/34* (2013.01); *A61L 15/44* (2013.01); *B32B 37/02* (2013.01); *B32B 37/10* (2013.01); *B32B 37/16* (2013.01); *B32B 2307/70* (2013.01); *B32B 2307/726* (2013.01); *B32B 2535/00* (2013.01); *Y10T 156/10* (2015.01)

(56) References Cited

U.S. PATENT DOCUMENTS

| | | | |
|---|---|---|---|
| 4,759,754 A | 7/1988 | Korpman | |
| 4,834,735 A * | 5/1989 | Alemany | A61F 13/533 428/213 |
| 5,078,710 A | 1/1992 | Suda et al. | |
| 5,334,176 A | 8/1994 | Buenger et al. | |
| 5,344,416 A | 9/1994 | Niihara | |
| 5,614,283 A | 3/1997 | Potnis et al. | |
| 5,650,214 A | 7/1997 | Anderson et al. | |
| 5,817,079 A * | 10/1998 | Bergquist | A61F 13/15626 428/299.1 |
| 6,060,636 A * | 5/2000 | Yahiaoui | A61L 15/20 604/367 |
| 6,100,442 A * | 8/2000 | Samuelsson | A61F 13/47227 604/385.01 |
| 6,153,209 A | 11/2000 | Vega et al. | |
| 6,350,711 B1 * | 2/2002 | Potts | A61F 13/15634 442/123 |
| 6,673,418 B1 * | 1/2004 | DeOlivera | A61F 13/474 428/141 |
| 6,673,982 B1 * | 1/2004 | Chen | A61F 13/4751 604/378 |
| 6,730,819 B1 | 5/2004 | Pesce | |
| 7,279,613 B2 * | 10/2007 | Nozaki | A61F 13/15203 604/379 |
| 9,161,869 B2 * | 10/2015 | Lee | A61F 13/8405 |
| 2001/0029141 A1 | 10/2001 | Mizutani et al. | |
| 2002/0049417 A1 | 4/2002 | Onishi et al. | |
| 2003/0088222 A1 | 5/2003 | Yoshimasa et al. | |
| 2003/0149410 A1 | 8/2003 | Kudo et al. | |
| 2003/0198784 A1 | 10/2003 | Mizutani et al. | |
| 2006/0004335 A1 * | 1/2006 | Wang | A61F 13/15658 604/368 |
| 2006/0184150 A1 | 8/2006 | Noel | |
| 2006/0276767 A1 | 12/2006 | Ueminami et al. | |
| 2007/0219515 A1 | 9/2007 | Marsh et al. | |
| 2007/0298213 A1 | 12/2007 | Noda et al. | |
| 2007/0298214 A1 | 12/2007 | Noda et al. | |
| 2007/0298220 A1 | 12/2007 | Noda et al. | |
| 2007/0298667 A1 | 12/2007 | Noda et al. | |
| 2007/0298671 A1 | 12/2007 | Noda et al. | |
| 2007/0299416 A1 | 12/2007 | Noda et al. | |
| 2008/0010795 A1 | 1/2008 | Mizutani et al. | |
| 2008/0044622 A1 | 2/2008 | Noda et al. | |
| 2008/0044628 A1 | 2/2008 | Noda et al. | |
| 2008/0045915 A1 | 2/2008 | Noda et al. | |
| 2008/0085399 A1 | 4/2008 | Noda et al. | |
| 2008/0119810 A1 * | 5/2008 | Kuroda | A61F 13/15707 604/379 |
| 2008/0132136 A1 | 6/2008 | Uematsu et al. | |
| 2008/0200894 A1 | 8/2008 | Gatto et al. | |
| 2009/0221978 A1 | 9/2009 | Gatto et al. | |
| 2009/0282660 A1 | 11/2009 | Noda et al. | |
| 2010/0069874 A1 | 3/2010 | Noda et al. | |
| 2010/0137824 A1 | 6/2010 | Uematsu et al. | |
| 2010/0151054 A1 * | 6/2010 | Nishioku | A61K 8/06 424/678 |
| 2010/0191207 A1 | 7/2010 | Oba et al. | |
| 2011/0130737 A1 * | 6/2011 | Sagisaka | A61F 13/4704 604/380 |
| 2011/0319851 A1 | 12/2011 | Kudo et al. | |
| 2012/0045620 A1 | 2/2012 | Oba et al. | |
| 2012/0123365 A1 * | 5/2012 | Pan | A61K 8/0208 604/367 |
| 2012/0141742 A1 | 6/2012 | Yamaguchi et al. | |
| 2012/0177889 A1 | 7/2012 | Uematsu et al. | |
| 2012/0196091 A1 | 8/2012 | Mizutani et al. | |
| 2012/0226250 A1 * | 9/2012 | Sato | A61F 13/51104 604/367 |
| 2013/0034686 A1 | 2/2013 | Mitsuno | |
| 2013/0137328 A1 | 5/2013 | Mitsuno | |
| 2013/0226123 A1 | 8/2013 | Kudo et al. | |
| 2014/0228793 A1 * | 8/2014 | Hashino | A61F 13/511 604/367 |
| 2015/0073370 A1 * | 3/2015 | Noda | A61F 13/539 604/378 |

FOREIGN PATENT DOCUMENTS

| | | |
|---|---|---|
| EP | 1250940 A1 | 10/2002 |
| EP | 1362568 | 11/2003 |
| EP | 1371379 A1 | 12/2003 |
| EP | 2036521 A1 | 3/2009 |
| EP | 2433602 A1 | 3/2012 |
| GB | 2262235 | 6/1993 |
| JP | S57-17081 | 4/1982 |
| JP | S64-34365 | 2/1989 |
| JP | S64-56051 | 3/1989 |
| JP | H01-158954 | 6/1989 |
| JP | 2152920 A | 6/1990 |
| JP | H02-229255 | 9/1990 |
| JP | H05-154176 | 6/1993 |
| JP | H06-5614 | 1/1994 |
| JP | 6502104 A | 3/1994 |
| JP | H07-84697 | 9/1995 |
| JP | H08-510665 | 11/1996 |
| JP | H08-322879 | 12/1996 |
| JP | H10-95810 | 4/1998 |
| JP | H10-510743 | 10/1998 |
| JP | H11-512643 | 11/1999 |
| JP | 2000-510376 | 8/2000 |
| JP | 3091283 | 9/2000 |
| JP | 2000-512886 | 10/2000 |
| JP | 2001-095845 | 4/2001 |
| JP | 2001-129019 | 5/2001 |
| JP | 2001-328191 | 11/2001 |
| JP | 2002-508693 | 3/2002 |
| JP | 3262172 | 3/2002 |
| JP | 2002528174 A | 9/2002 |
| JP | 2002537904 A | 11/2002 |
| JP | 2003-024372 | 1/2003 |
| JP | 2003-052750 | 2/2003 |
| JP | 2004-500908 | 1/2004 |
| JP | 2004-049529 | 2/2004 |
| JP | 2005-504591 | 2/2005 |
| JP | 2005-095759 | 4/2005 |
| JP | 2005193001 A | 7/2005 |
| JP | 2005-525134 | 8/2005 |
| JP | 2006501022 A | 1/2006 |

(56) References Cited

FOREIGN PATENT DOCUMENTS

| | | |
|---|---|---|
| JP | 2006-510456 | 3/2006 |
| JP | 2006-115996 | 5/2006 |
| JP | 2006-255051 | 9/2006 |
| JP | 2006280526 A | 10/2006 |
| JP | 200714705 A | 1/2007 |
| JP | 2007-509695 | 4/2007 |
| JP | 2008-002034 | 1/2008 |
| JP | 2008-023311 | 2/2008 |
| JP | 2008-023365 | 2/2008 |
| JP | 2008-025080 | 2/2008 |
| JP | 2008-025081 | 2/2008 |
| JP | 2008-025082 | 2/2008 |
| JP | 2008-025083 | 2/2008 |
| JP | 2008-025084 | 2/2008 |
| JP | 2008-025085 | 2/2008 |
| JP | 2008-029830 | 2/2008 |
| JP | 2008-503323 | 2/2008 |
| JP | 200825078 A | 2/2008 |
| JP | 200825079 A | 2/2008 |
| JP | 200829830 A | 2/2008 |
| JP | 2008-61761 A | 3/2008 |
| JP | 2008-138340 | 6/2008 |
| JP | 2008-144322 | 6/2008 |
| JP | 2008529721 A | 8/2008 |
| JP | 2008229032 A | 10/2008 |
| JP | 2008229033 A | 10/2008 |
| JP | 2008237569 A | 10/2008 |
| JP | 2008-264084 | 11/2008 |
| JP | 2008-266813 | 11/2008 |
| JP | 2008-541943 | 11/2008 |
| JP | 2008-307179 | 12/2008 |
| JP | 20095767 A | 1/2009 |
| JP | 2009-030218 | 2/2009 |
| JP | 2009-201878 | 9/2009 |
| JP | 2009-297048 | 12/2009 |
| JP | 201088822 A | 4/2010 |
| JP | 2010518918 A | 6/2010 |
| JP | 2010-148708 | 7/2010 |
| JP | 2010526629 A | 8/2010 |
| JP | 2010-285735 | 12/2010 |
| JP | 2010279568 A | 12/2010 |
| JP | 2011-038211 | 2/2011 |
| JP | 2011-074515 | 4/2011 |
| JP | 2011-080178 | 4/2011 |
| JP | 201167484 A | 4/2011 |
| JP | 201172650 A | 4/2011 |
| JP | 2011510801 A | 4/2011 |
| JP | 2011-104059 | 6/2011 |
| JP | 2011-120696 | 6/2011 |
| JP | 4693847 | 6/2011 |
| JP | 2011104001 A | 6/2011 |
| JP | 2011226010 A | 11/2011 |
| JP | 2011226011 A | 11/2011 |
| JP | 2012-050626 | 3/2012 |
| JP | 5122007 | 1/2013 |
| WO | 9301781 A1 | 2/1993 |
| WO | 94/27539 | 12/1994 |
| WO | 96/19173 | 6/1996 |
| WO | 98/55158 | 12/1998 |
| WO | 99/00093 | 1/1999 |
| WO | 99/29274 | 6/1999 |
| WO | 0024351 A1 | 5/2000 |
| WO | 01/045757 | 6/2001 |
| WO | 03/017900 | 3/2003 |
| WO | 03/028776 | 4/2003 |
| WO | 2004030713 A1 | 4/2004 |
| WO | 2004/058119 | 7/2004 |
| WO | 2005/044164 | 5/2005 |
| WO | 2006/009996 | 1/2006 |
| WO | 2006/130646 | 12/2006 |
| WO | 2008/072675 | 6/2008 |
| WO | 2008101163 A2 | 8/2008 |
| WO | 2008139425 A1 | 11/2008 |
| WO | 2008/149771 | 12/2008 |
| WO | 2009102837 A2 | 8/2009 |
| WO | 2011/065247 A1 * | 6/2011 ............ A61F 13/511 |
| WO | 2012/133724 | 10/2012 |

OTHER PUBLICATIONS

International Search Report dated Mar. 19, 2013 in corresponding International Application No. PCT/JP2012/082087.
International Search Report dated Mar. 12, 2013 in corresponding International Application No. PCT/JP2012/082104.
International Search Report dated Mar. 19, 2013 in corresponding International Application No. PCT/JP2013/054382.
International Search Report dated May 21, 2014 in corresponding International Application No. PCT/JP2013/054796.
International Search Report dated Jul. 2, 2013 in corresponding International Application No. PCT/JP2013/058860.
International Search Report dated Jul. 2, 2013 in corresponding International Application No. PCT/JP2013/058861.
International Search Report dated Mar. 19, 2013 in corresponding International Application No. PCT/JP2012/082078.
International Search Report dated Jul. 2, 2013 in corresponding International Application No. PCT/JP2013/058862.
International Search Report dated Jun. 18, 2013 in corresponding International Application No. PCT/JP2013/058855.
International Search Report dated May 14, 2013 in corresponding International Application No. PCT/JP2013/058836.
International Search Report dated May 21, 2013 in corresponding International Application No. PCT/JP2013/058859.
International Search Report dated Jan. 8, 2013, corresponds to International Application No. PCT/JP2012/075583.
Written Opinion dated Jul. 3, 2012, corresponds to International Application No. PCT/JP2012/058499.
Reply to Written Opinion dated Jan. 30, 2013, corresponds to International Application No. PCT/JP2012/058499.
International Search Report dated Jul. 17, 2012, corresponds to International Application No. PCT/JP2012/061505.
International Search Report dated Mar. 26, 2013, corresponds to International Application No. PCT/JP2012/082977.
Atsushi Fujita, "Prediction of Organic Compounds and Organic Conceptual Diagram", Kagaku no Ryoiki (Region of Chemistry), Oct. 1957, p. 719-725, vol. 11, No. 10.

* cited by examiner

Fig.5
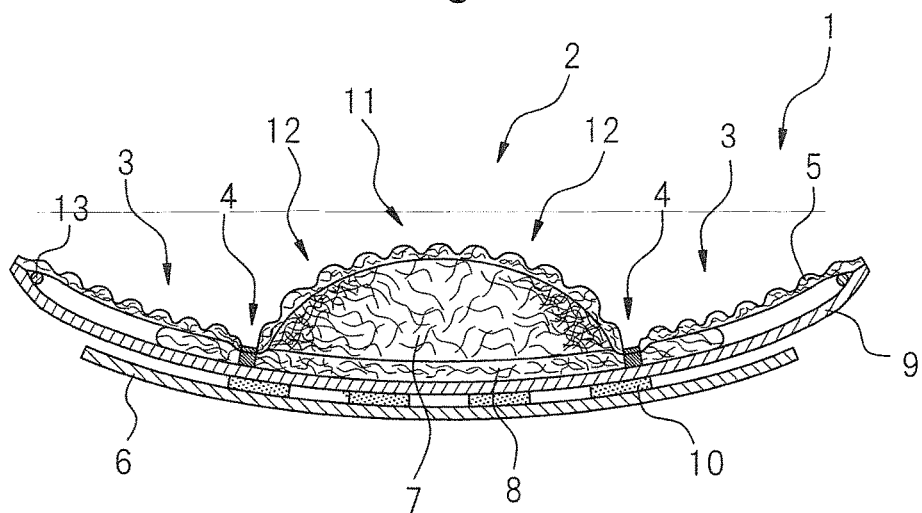
Fig.6
(a)
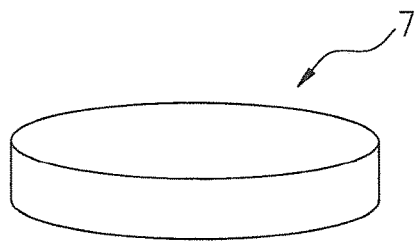
(b)
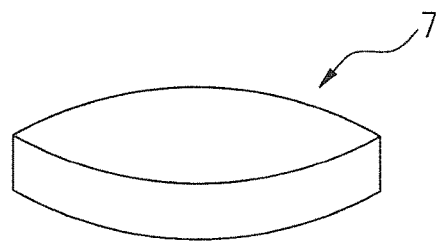
(c)
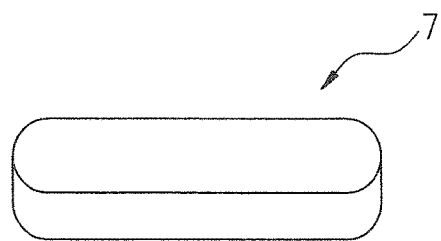

200 μm

Fig.8
(a)
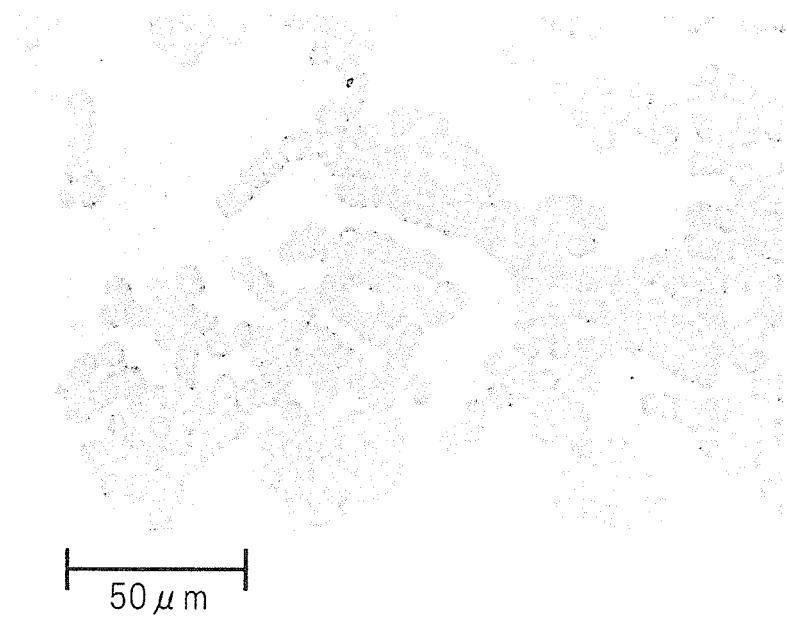
50 μm
(b)
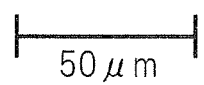
50 μm

ABSORBENT ARTICLE HAVING A DOMED SECTION AND METHOD OF MANUFACTURING SAME

RELATED APPLICATIONS

The present application is a National Phase of International Application Number PCT/JP2012/082977, filed Dec. 19, 2012, which claims priority to Japanese Application Number 2011-289970, filed Dec. 28, 2011.

TECHNICAL FIELD

The present disclosure relates to an absorbent article and to a method for producing it.

BACKGROUND ART

Absorbent articles such as sanitary napkins are known that are provided with protrusions exhibiting cushioning properties on the skin contact side of the top sheet, for suitable fitting with the body of the wearer. Providing protrusions on the skin contact side of the top sheet allows more suitable fitting to the body of the wearer to help prevent fluid leakage even when the body of the wearer has moved.

For example, PTL 1 describes an absorbent article, the object being to provide an absorbent article exhibiting satisfactory cushioning properties even when the protrusions are under low load, an excellent fitting property and feel during wear, and resistance to leakage. The absorbent article described in PTL 1 has the following construction: An absorbent article comprising a front sheet, a back sheet and an absorbing layer disposed between both sheets, the absorbent article being formed in an essentially longitudinal manner, and having protrusions protruding toward the skin side of the wearer at the center section in the widthwise direction of the absorbent article, wherein the protrusions internally comprise an upper cushion layer situated adjacent to the front sheet and a lower cushion layer located under the upper cushion layer, a lower absorbing layer being situated on the non-skin contact side of the lower cushion layer, and the upper cushion layer being more easily deformable under pressure in the thickness direction, than the lower cushion layer.

Also, PTL 2 describes an absorbent article, the object being to provide an absorbent article with excellent cushioning properties, having protrusions that exhibit a satisfactory fitting property and flexibly deform to follow movement of the skin of the wearer, and having low fluid spread and resistance to wet-back. The absorbent article described in PTL 2 has the following construction: An absorbent article comprising a front sheet, a back sheet and an absorbing layer between them, wherein the absorbing layer comprises a lower absorbing layer, an upper absorbing layer located further toward the front sheet side than the lower absorbing layer and having a smaller size than the lower absorbing layer, and a cushion layer disposed between the lower absorbing layer and the upper absorbing layer, there being formed protrusions protruding toward the front sheet side by the front sheet, the upper absorbing layer and the cushion layer, at the center section in the widthwise direction of the absorbent article, the cushion layer is made of a fiber aggregate composed mainly of hydrophilic synthetic fiber, the density $\rho U$ of the upper absorbing layer, the density $\rho C$ of the cushion layer and the density $\rho D$ of the lower absorbing layer satisfy the relationship $\rho C < \rho U < \rho D$ under non-pressure conditions, and the density $\rho UP$ of the upper absorbing layer, the density $\rho CP$ of the cushion layer and the density $\rho DP$ of the lower absorbing layer satisfy the relationships $\rho UP \leq \rho CP \leq \rho DP$ and $\rho UP < \rho DP$ under pressure conditions.

CITATION LIST

Patent Literature

[PTL 1] Japanese Unexamined Patent Publication No. 2008-229032
[PTL 2] Japanese Unexamined Patent Publication No. 2008-229033

SUMMARY OF INVENTION

Technical Problem

With the absorbent article described in PTL 1, however, increasing the cushioning properties of the protrusions to improve the feel during wear results in higher collapsability of the protrusions, and especially the cushion layer, upon wetting and creation of voids between it and the body of the wearer, leading to increased leakage. With the rigidity of the protrusions, and especially the cushion layer, is increased to counter periods of wetness, the protrusions become less fittable on the body of the wearer, and particularly the labia minora and labia majora, during periods of dryness, and voids are created between the protrusions and the body of the wearer, likewise leading to greater leakage.

With the absorbent article described in PTL 2, the presence of the upper absorbing layer on the uppermost layer of the protrusions results in a poorer fit of the protrusions on the body of the wearer, and particularly the labia minora and labia majora, during periods of dryness, and this creates voids between the protrusions and the body of the wearer, leading to increased leakage.

It is therefore an object of the present disclosure to provide an absorbent article that satisfactorily fits with the excretory opening of the wearer, and especially the labia minora, both during periods of dryness before absorption of menstrual blood and during periods of wetness after menstrual blood has been absorbed, and that is resistant to leakage.

Solution to Problems

As a result of diligent research directed toward solving the problems described above, the present inventors have found an absorbent article comprising a liquid-permeable top sheet, a liquid-impermeable back sheet and an absorbent body between the liquid-permeable top sheet and liquid-impermeable back sheet, wherein the absorbent article has in the excretory opening contact region a domed section that protrudes in the thickness direction of the absorbent article, the domed section includes part of the top sheet and a cushion section disposed between the top sheet and the absorbent body, and the domed section has a center section and an outer peripheral section surrounding the center section, and the density of the cushion section at the outer peripheral section is higher than the density of the cushion section at the center section.

Advantageous Effects of Invention

The absorbent article of the present disclosure satisfactorily fits with the excretory opening of the wearer, and especially the labia minora, both during periods of dryness before absorption of menstrual blood and during periods of wetness after menstrual blood has been absorbed, and is resistant to leakage.

BRIEF DESCRIPTION OF DRAWINGS

FIG. 5 is an end view of the absorbent article 1 shown in FIG. 1, along edge Y-Y of FIG. 2.

FIG. 6 is a diagram showing an example of the shape of a cushion section before it is incorporated into an absorbent article.

FIG. 8 is a pair of photomicrographs of menstrual blood containing and not containing a blood modifying agent.

DESCRIPTION OF EMBODIMENTS

The absorbent article of the present disclosure will now be explained in detail.

Figure 1:
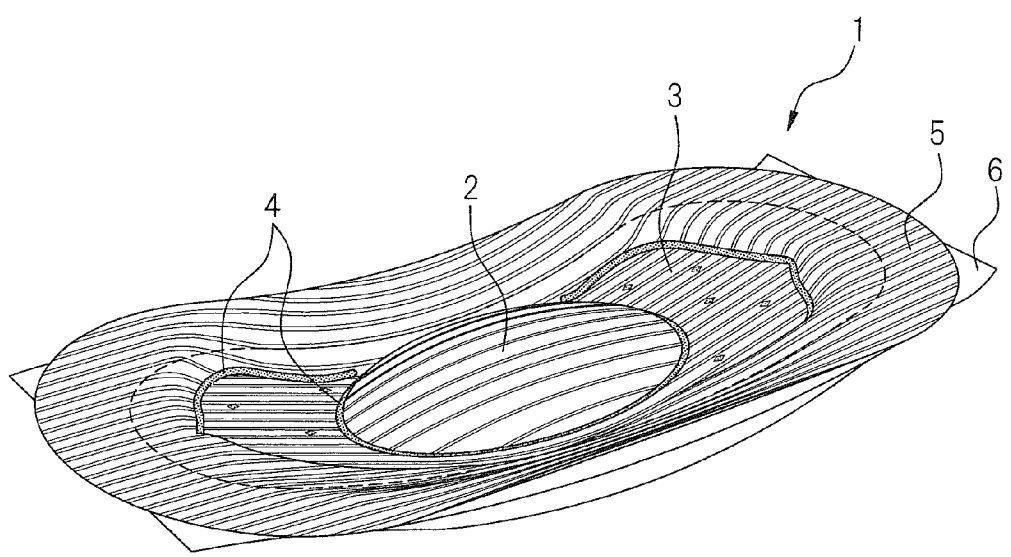
FIG. 1 is a perspective view of an absorbent article according to an embodiment of the present disclosure.

FIG. 1 is a perspective view of an absorbent article according to an embodiment of the present disclosure. The absorbent article 1 shown in FIG. 1 is a sanitary napkin. In the absorbent article 1 shown in FIG. 1, the right side corresponds to the front of the wearer while the left side corresponds to the back of the wearer, and the absorbent article 1 shown in FIG. 1 has a shape with essentially longitudinal symmetry and bilateral symmetry.

The absorbent article 1 shown in FIG. 1 comprises a liquid-permeable top sheet 5, a liquid-impermeable back sheet (not shown), and an absorbent body (not shown) between the liquid-permeable top sheet 5 and liquid-impermeable back sheet. Also shown in FIG. 1 are a compressed section 4, and a detaching portion 6 anchored to the back sheet.

The absorbent article 1 shown in FIG. 1 has a domed section 2 that protrudes in the thickness direction of the absorbent article 1 in the excretory opening contact region.

In the absorbent article 1 shown in FIG. 1, the top sheet 5 has a plurality of ridge-furrow structures extending in the lengthwise direction on the skin contact surface, the borders between the ridges and furrows being illustrated as solid lines for convenience in FIG. 1. In the absorbent article 1 shown in FIG. 1, the wide regions surrounded by two solid lines are the ridges and the narrow regions surrounded by two solid lines are the furrows, and in the absorbent article 1 shown in FIG. 1, a plurality of ridges and a plurality of furrows are alternately arranged in the widthwise direction of the absorbent article 1. A perimeter section 3 surrounding the domed section 2 is also shown in FIG. 1.

As used herein, the direction perpendicular to the lengthwise direction of the absorbent article will also be referred to simply as "widthwise direction".

Also as used herein, "domed section" refers to a section including the top sheet and the cushion section, and since it generally has the maximum thickness of the absorbent article, its thickness decreases toward the outer peripheral section.

As used herein, "center section" refers to the section that includes the part of the domed section at the point where the thickness is at the maximum. The thickness is the thickness from the clothing contact surface of the back sheet.

The "center section", as it relates to the domed section, is the region of preferably between 0 and about 50%, more preferably between 0 and about 40%, and even more preferably between 0 and about 30%, of the distance from the point of maximum thickness to the outer edge of the domed section.

Figure 2:
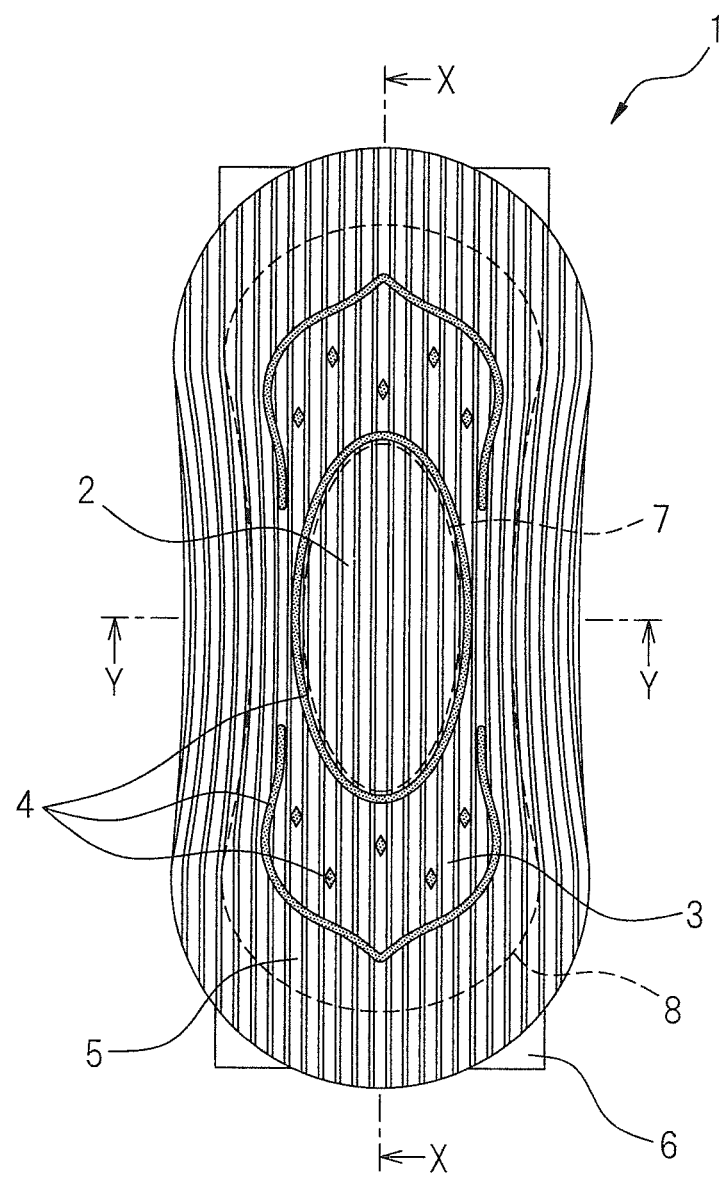
FIG. 2 is a front view of the absorbent article 1 shown in FIG. 1.

FIG. 2 is a front view of the absorbent article 1 shown in FIG. 1, as observed from the skin contact side of the top sheet 1. In the absorbent article 1 shown in FIG. 2, the upper end corresponds to the front of the wearer, and the lower end corresponds to the back of the wearer. The absorbent article 1 shown in FIG. 2 comprises a liquid-permeable top sheet 5, a liquid-impermeable back sheet (not shown), and an absorbent body 8 between the liquid-permeable top sheet 5 and liquid-impermeable back sheet. The absorbent article 1 shown in FIG. 2 also has a domed section 2 that protrudes in the thickness direction of the absorbent article 1 in the region in contact with the excretory opening, and especially the labia minora. The domed section 2 includes part of the top sheet 5, and a cushion section 7 situated between the top sheet 5 and the absorbent body 8. Also shown in FIG. 2 are a perimeter section 3 surrounding the domed section 2, a compressed section 4, and a detaching portion 6 anchored to the back sheet.

Figure 3:
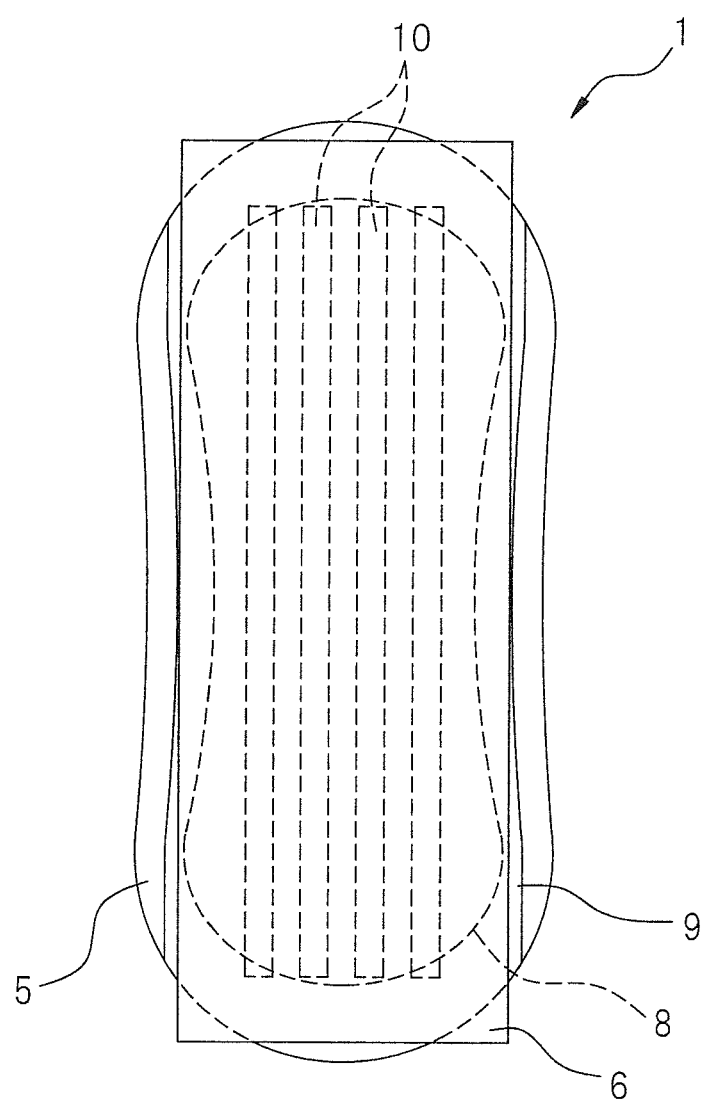
FIG. 3 is a rear view of the absorbent article 1 shown in FIG. 1.

FIG. 3 is a rear view of the absorbent article 1 shown in FIG. 1, as observed from the clothing contact surface side of the back sheet 5. In the absorbent article 1 shown in FIG. 3, the upper end corresponds to the front of the wearer, and the lower end corresponds to the back of the wearer. In the absorbent article 1 shown in FIG. 3, an anchoring part 10 is coated on the clothing contact surface of the liquid-impermeable back sheet 9, and the detaching portion 6 is anchored to the anchoring part 10. During use, the wearer may use the absorbent article by detaching the detaching portion 6 and anchoring the anchoring part 10 to the clothing.

Figure 4:
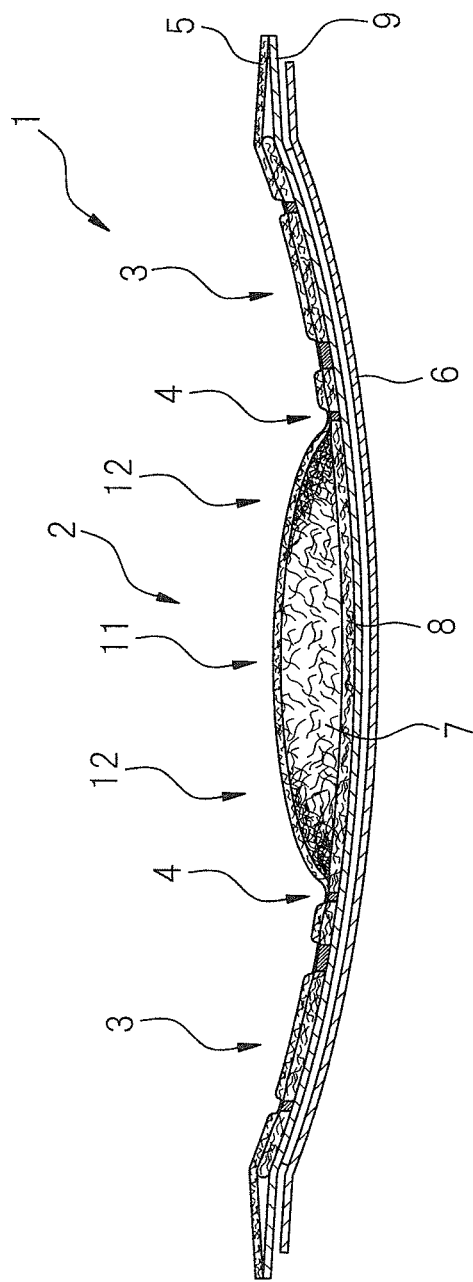
FIG. 4 is an end view of the absorbent article 1 shown in FIG. 1, along edge X-X of FIG. 2.

FIG. 4 is an end view of the absorbent article 1 shown in FIG. 1, along edge X-X of FIG. 2. In the absorbent article 1 shown in FIG. 4, the right side corresponds to the front of the wearer, and the left side corresponds to the back of the wearer. In the absorbent article 1 shown in FIG. 4, a liquid-impermeable back sheet 9, absorbent body 8 and liquid-permeable top sheet 5 are layered in that order from the bottom, and a cushion section 7 is disposed between the absorbent body 8 and the liquid-permeable top sheet 5, in the excretory opening contact region. The domed section 2 includes part of the top sheet 5 and the cushion section 7, and the absorbent article 1 has a compressed section 4 formed by compressing the top sheet 5 and absorbent body 8 near the outer edge of the cushion section 7, and more specifically, outside the cushion section.

In the absorbent article 1 shown in FIG. 4, the liquid-permeable top sheet 5 has a plurality of ridge-furrow structures on the skin contact surface. As shown in FIG. 4, the density of the cushion section 7 at the outer peripheral section 12, in the domed section 2 of the absorbent article 1, is higher than the density of the cushion section 7 at the center section 11.

FIG. 5 is an end view of the absorbent article 1 shown in FIG. 1, along edge Y-Y of FIG. 2. The absorbent article 1 shown in FIG. 5 has a compressed section 4 formed by compressing the top sheet 5 and absorbent body 8 near the outer edge of the cushion section 7, and more specifically, outside the cushion section. As shown in FIG. 5, the absorbent article 1 has a plurality of ridge-furrow structures on the skin contact surface. As shown in FIG. 5, the density of the cushion section 7 at the outer peripheral section 12, in the domed section 2 of the absorbent article 1, is higher than the density of the cushion section 7 at the center section 11. An elastic member 13 is also shown in FIG. 5.

In this absorbent article, the material of the cushion section is not particularly restricted and may be made of a material such as, for example, a fiber-containing or non-fiber-containing material.

Examples of fiber-containing materials include those that contain natural fibers, chemical fibers or both, and preferably a plurality of the fiber intersections are heat-fused. Heat-fusing the fiber intersections can provide excellent shape stability of the cushion section, and therefore the domed section, even after menstrual blood has been absorbed.

The fiber-containing material preferably comprises approximately 50 to 100 mass % and more preferably approximately 70 to 100 mass % of thermoplastic chemical fibers, in order to accomplish heat fusion between the fibers.

The starting material for the thermoplastic chemical fibers may be polyethylene (PE), polypropylene (PP), polyethylene terephthalate (PET), PE and PP graft polymer, or the like, and the thermoplastic chemical fibers may be single filaments or composite fibers, such as core-sheath fibers, heat-shrinkable fibers or heat-extendable fibers. In consideration of facilitating uptake of menstrual blood and inhibiting rewet-back, the thermoplastic chemical fibers may be kneaded with or coated with a hydrophilic agent, water-repellent agent or the like. Corona treatment or plasma treatment of the thermoplastic chemical fibers can render the thermoplastic chemical fibers hydrophilic.

In order to increase the whiteness of the cushion section, an inorganic filler such as titanium oxide, barium sulfate or calcium carbonate may be added to the fibers. When the fibers composing the cushion section are core-sheath fibers, the inorganic filler may be added to the core and/or sheath.

When the cushion section is a fiber-containing material, the fibers composing the fiber-containing material are preferably composite fibers rather than single filaments, and more preferably core-sheath fibers comprising polyethylene in the sheath, from the viewpoint of compression recoverability.

The composite fibers may be core-sheath fibers wherein the melting point of the core component is higher than the melting point of the sheath component, eccentric core-sheath fibers, or side-by-side fibers wherein the two components have different melting points. Also, when the cushion section is a fiber-containing material, the cushion section may comprise irregularly shaped fibers such as hollow fibers, flat fibers, Y-shaped fibers or C-shaped fibers, solid crimped fibers such as latent crimped or developed crimped fibers, or split fibers that have been split by a physical load such as a water stream, heat, embossing or the like.

When the cushion section is a fiber-containing material, the fibers composing the cushion section preferably have a size of about 1.1 to about 8.8 dtex, from the viewpoint of facilitating uptake of menstrual blood and improved feel on the skin.

Examples of natural fibers include cellulose such as ground pulp or cotton, regenerated cellulose such as rayon or fibril rayon, and semi-synthetic cellulose such as acetate or triacetate, with ground pulp being preferred from the viewpoint of low cost and easier shaping. If the cushion section contains cellulose, it will be possible to inhibit leakage when it is difficult to apply body pressure to the domed section, due to sleeping posture, etc. If the cushion section is formed of 100% thermoplastic chemical fibers, menstrual blood will flow on the outer surface of the top sheet, often resulting in leakage.

When the cushion section is a fiber-containing material, the cushion section can be formed by web forming, in a dry system (carding method, spunbond method, meltblown method, airlaid method or TOW) or a wet system, or a combination thereof. The method for bonding the cushion section may be, for example, thermal bonding, needle punching, chemical bonding, hydroentangling or the like.

Examples of non-fiber-containing materials include elastomers, and continuous foam materials such as foamed polyethylene. Specific examples of elastomers include polyester-based, urethane-based, olefin-based, styrene-based and polyamide-based thermoplastic elastomers, and low-density polyethylene or ethylene-α-olefin copolymer using metallocene catalysts, as well as combinations of the foregoing. These polyester-based elastomers include those comprising an aromatic polyester in the hard segment and an amorphous polyether or aliphatic polyester in the soft segment.

A "continuous foam material" is an open foam material having open foam cells. A closed foam material without open foam cells will result in poor permeation of menstrual blood through the interior of the cushion section, and inferior liquid permeability.

Examples of urethane-based elastomers include polyurethanes comprising polyesters, low molecular glycol, methylene bisphenyl isocyanate or the like as thermoplastic elastomers. Examples of olefin-based elastomers include random copolymers of ethylene and α-olefin, and random copolymers of ethylene, α-olefins and dienes. Examples of styrene-based elastomers include block copolymers such as SEBS, SIS, SEPS and SBS. These polyamide-based elastomers may include nylon as the hard segment, and a polyester or polyol as the soft segment.

The non-fiber-containing material may include high-density polyethylene, low-density polyethylene, linear low-density polyethylene or the like for shaping stability. The non-fiber-containing material may also include an antiblocking agent, ultraviolet absorber, thickening/branching agent, delustering agent, coloring agent, or different types of modifiers. In consideration of facilitating uptake of menstrual blood and inhibiting rewet-back, the non-fiber-containing material may be kneaded with or coated with a hydrophilic agent, water-repellent agent or the like. Corona treatment or plasma treatment of the non-fiber-containing material can render the non-fiber-containing material hydrophilic.

The following is conjectured to be the reason for the effect of the disclosure of the present claim 1, i.e. the effect by which the domed section satisfactorily fits with the excretory opening of the wearer, and especially the labia minora, both during periods of dryness before absorption of menstrual blood and during periods of wetness after menstrual blood has been absorbed, and provides resistance to leakage.

The labia minora of an adult female does not have a uniform shape and it undergoes little shape deformation when the body is moved, especially compared to the labia majora, though with differences from individual to individual. Also, deformation of the labia majora during body movement varies greatly depending on the body type of the woman, the labia majora tending to deform much more easily during body movement in slightly overweight women.

In the absorbent article of the present disclosure, a domed section is provided in the excretory opening contact region, and the density of the cushion section forming the domed section differs between the outer peripheral section of the domed section and the center section, the density of the cushion section at the outer peripheral section being higher than the density of the cushion section at the center section. Thus, the cushion section that has relatively low density at the center section of the domed section has low rigidity, and when it contacts with the labia minora, it deforms along the shape of the labia minora allowing it to embed the labia minora. However, the cushion section that has relatively high density at the outer peripheral section of the domed section has high rigidity, and it can continue to contact with the border between the labia minora and the labia majora, or with the labia majora, during periods of dryness before absorption of menstrual blood. Also, the cushion section that has relatively high density at the outer peripheral section of the domed section has high compression recoverability, and therefore it can continue to contact with the complex-shaped excretory opening even during periods of wetness after menstrual blood has been absorbed.

As used herein, "excretory opening contact region" refers to the region bordering the excretory opening of the wearer, and "excretory opening" refers primarily to the labia minora, though not precluding that the outer peripheral section of the domed section borders with the labia majora.

Also, since the center section of the domed section is easily compressed, it deforms with depressions along the shape of the labia minora of the wearer during use, embedding the labia minora, so that the top sheet closely contacts with the vaginal opening, and it is possible to prevent excessive spread of menstrual blood on the top sheet.

Also, since the top sheet closely contacts with the vaginal opening, the distance between the vaginal opening and the absorbent body is minimal during use, and when the cushion section is composed mainly of thermoplastic chemical fiber, menstrual blood passes through the top sheet and cushion section without diffusing in the planar directions during initial absorption of menstrual blood, and can rapidly migrate into the absorbent body. Once a passage is formed for menstrual blood, the region becomes hydrophilicized, and therefore even during a second or later absorption of menstrual blood, the menstrual blood passes through the top sheet and cushion section and can rapidly migrate into the absorbent body.

Furthermore, even in cases where body pressure is applied and the bulk of the cushion section is temporarily reduced, such that a large amount of menstrual blood pools in the cushion section with the reduced bulk, the bulk of the cushion section rapidly recovers when the body pressure is weakened, starting with the outer peripheral section of the domed section, allowing menstrual blood to rapidly migrate into the absorbent body.

It is a feature of the absorbent article of the present disclosure that the density of the cushion section at the outer peripheral section of the domed section is higher than the density of the cushion section at the center section of the domed section, but in an absorbent article according to one embodiment of the present disclosure, this feature is achieved by having compressed sections formed by compressing at least the top sheet and absorbent body, near the outer edge of the cushion section, for example. By compressing at least the top sheet and the absorbent body in such a manner that the outer edge of the cushion section is compressed by tensile force of the compressed top sheet and absorbent body, creating a reduced thickness there, it is possible to increase the density of the cushion section at the outer peripheral section of the domed section above the density of the cushion section at the center section of the domed section. Also, since the degree of compression of the cushion section is low at the center section of the domed section and the thickness is not reduced as much as the outer peripheral section, the density of the cushion section does not easily increase.

Specific examples of cases where compressed sections are provided near the outer edge of the cushion section, formed by compressing at least the top sheet and the absorbent body, include (i) an example in which compressed sections are formed by compressing the top sheet and absorbent body on the outside of the cushion section, and (ii) an example in which compressed sections are formed by compressing the top sheet, cushion section and absorbent body on the outer edge of the cushion section.

As absorbent articles according to different embodiments of the present disclosure, there may be mentioned (i) an absorbent article that is formed by compressing the outer edge of the cushion section, and then layering the liquid-impermeable back sheet, absorbent body, cushion section and top sheet in that order, (ii) an absorbent article that is formed by layering the cushion section on the absorbent body, compressing the outer edge of the cushion section and the absorbent body together, and then layering the liquid-impermeable back sheet, compressed members and liquid-permeable top sheet in that order, and (iii) an absorbent article that is formed by layering the cushion section on the liquid-permeable top sheet, compressing the outer edge of the cushion section and the top sheet together, and then layering the liquid-impermeable back sheet, absorbent body and compressed members in that order.

With compressed sections formed by compressing at least the top sheet and absorbent body near the outer edge of the cushion section, it is possible during periods of wetness after menstrual blood has been absorbed, for example, to minimize detachment of the top sheet from the absorbent body and to maintain the height of the density of the cushion section at the outer peripheral section of the domed section.

As used herein, the phrase "near the outer edge", as it relates to the cushion section, is a concept including not only the outer edge of the cushion section, but also an area inside the outer edge of the cushion section and an area outside the outer edge of the cushion section. Also, "near" means a range of preferably ±15%, more preferably ±10% and even more preferably ±5%, of the distance from the center of the cushion section to the outer edge of the cushion section, in the planar direction of the absorbent article.

The "center" of the cushion section is the center in the lengthwise direction and the widthwise direction of the absorbent article.

The embodiments shown in FIGS. 1 to 5 each have compressed sections formed by continuously compressing the top sheet and absorbent body on the outside of the cushion section, but in an absorbent article according to a different embodiment of the present disclosure, compressed sections may be present that are formed by intermittently compressing the top sheet and absorbent body on the outside of the cushion section. In an absorbent article according to yet another embodiment of the disclosure, compressed sections may be present that are formed by continuously or intermittently compressing the top sheet, the cushion section and the absorbent body at the edge of the cushion section, and in an absorbent article according to yet another embodiment of the disclosure, compressed sections may be present that are formed by continuously or intermittently compressing only the cushion section at the edge of the cushion section.

The shape of the cushion section before it is incorporated into the absorbent article is not particularly restricted so long as an absorbent article is formed in which the density of the cushion section at the outer peripheral section of the domed section is higher than the density of the cushion section at the center section of the domed section after the cushion section has been incorporated, and for example, the projected form in the thickness direction of the absorbent article may have a shape similar to the labia minora, such as roughly circular, roughly elliptical, roughly rounded rectangular, or a figure surrounded by two arcs.

The cushion section may also have a constant thickness in the thickness direction of the absorbent article, or it may have a thickness that increases toward the outer edges from the center, or it may have a thickness that decreases toward the outer edges form the center. When the thickness of the cushion section decreases from the center toward the outer edges, in cases where the absorbent body and top sheet have been compressed, it will often be difficult for the density of the cushion section at the outer peripheral section of the domed section to be increased above the density of the cushion section at the center section of the domed section, and therefore it is preferred for the cushion section to have a constant thickness, or for the thickness to increase from the center toward the outer edges.

The cushion section may also have a different basis weight at different locations.

FIG. 6 is a diagram showing an example of the shape of a cushion section before it is incorporated into an absorbent article. FIG. 6(a) shows a cushion section before being incorporated into an absorbent article, wherein the projected form in the thickness direction of the absorbent article is roughly elliptical and the thickness is constant, FIG. 6(b) shows a cushion section before being incorporated into an absorbent article, wherein the projected form in the thickness direction of the absorbent article is a figure surrounded by two arcs, and the thickness is constant, and FIG. 6(c) shows a cushion section before being incorporated into an absorbent article, wherein the projected form in the thickness direction of the absorbent article is a roughly rounded rectangular shape, and the thickness is constant.

The density of the cushion section at the center section of the domed section is preferably about 0.001 to 0.1 g/cm$^3$, more preferably about 0.005 to about 0.08 g/cm$^3$, and even more preferably about 0.01 to about 0.05 g/cm$^3$. If the density is less than about 0.001 g/cm$^3$, the compression recoverability will tend to be inadequate during periods of wetness after menstrual blood has been absorbed, and if the density is greater than about 0.1 g/cm$^3$, it will tend to deform along the labia minora of the wearer, resulting in more difficult fitting to the labia minora.

The density of the cushion section at the center section and outer peripheral section of the domed section can be measured in the following manner.

(1) A two-dimensional laser displacement gauge is used to measure the thickness t (cm) of the cushion section at the measuring location. An example of such a two-dimensional laser displacement gauge is the LJ-G Series high precision two-dimensional laser displacement gauge (Model: LJ-G030) by Keyence Corp. The thickness of the cushion section at the measuring location can be calculated by subtracting the thickness of the absorbent article in the region other than the cushion section, i.e. at the perimeter section surrounding the domed section, from the thickness of the absorbent article at the measuring location.

(2) The cushion section is removed from the absorbent article and its basis weight b (g/m$^2$) is measured. When the basis weight of the cushion section differs depending on the location, an approximately 15 mm×15 mm sample is taken centered on the measuring location, and its basis weight b (g/m$^2$) is measured.

(3) The density d (g/cm$^3$) is calculated by the following formula:

$$d=b/(10,000\times t).$$

As indicated by this formula, if the basis weight of the cushion section is constant, the ratio of the density at locations other than the cushion section can be compared by the thickness alone. That is, when the basis weight of the cushion section is constant, a lower thickness of the cushion section represents a higher density of the cushion section.

In the absorbent article of the present disclosure, the density of the cushion section at the outer peripheral section of the domed section is higher than the density of the cushion section at the center section of the domed section, and preferably it is about 1.1 to about 5.0 times higher than the density of the cushion section at the center section of the domed section, more preferably about 1.2 to about 4.0 times higher than the density of the cushion section at the center section of the domed section, and even more preferably about 1.5 to about 3.0 times higher than the density of the cushion section at the center section of the domed section. If the proportion is less than about 1.1 times higher, the compression recoverability of the cushion section at the outer peripheral section of the domed section will tend to be inadequate during periods of wetness, and if the proportion is greater than about 5 times higher, the rigidity of the cushion section at the outer peripheral section of the domed section will be increased, tending to leave the wearer with a feeling of the presence of a foreign object.

In the absorbent article of the present disclosure, the maximum thickness of the cushion section is preferably about 3 to about 30 mm, more preferably about 4 to about 20 mm, and even more preferably about 5 to about 10 mm. If the maximum thickness of the cushion section is within this range, it will fit the excretory opening of the wearer, and especially the labia minora, during wearing, thus helping to reduce leakage.

As used herein, the term "maximum thickness" as it relates to the domed section of the cushion section, is the thickness at the thickest section of the cushion section and domed section.

The cushion section has a length of preferably about 30 to about 300 mm, more preferably about 40 to about 250 mm and even more preferably about 50 to about 100 mm in the lengthwise direction of the absorbent article, and a length of preferably about 10 to about 100 mm, more preferably about 20 to about 70 mm and even more preferably about 25 to about 50 mm in the widthwise direction of the absorbent article. If the size of the cushion section is within this range, the domed section will fit the excretory opening of the wearer, and especially the labia minora, during wearing, thus allowing leakage to be minimized. If the size of the cushion section is smaller than this range, the domed section will fail to fit the excretory opening of the wearer, and especially the labia minora, tending to result in leakage, while if the size of the cushion section is larger than this range, an uncomfortable feeling will tend to be noticed during wearing, or a gap will tend to form between the labia minora, resulting in easier leakage.

As used herein, unless otherwise specified, the term "lengthwise direction" means the lengthwise direction of the absorbent article, and the term "widthwise direction" means the widthwise direction of the absorbent article, while the direction of "thickness" means the thickness direction of the absorbent article.

The cushion section in the absorbent article of the present disclosure has a basis weight of preferably about 50 to about 1,000 g/m², more preferably about 100 to 500 g/m², and even more preferably about 150 to about 300 g/m². If the basis weight is within this range, the domed section will not collapse even during periods of wetness after menstrual blood has been absorbed, and the domed section will fit the excretory opening of the wearer, and especially the labia minora, thus reducing leakage.

The cushion section preferably retains at least about 50% of its maximum thickness, more preferably it retains at least about 60% of its maximum thickness and even more preferably it retains at least about 70% of its maximum thickness, after absorption of 2 g of horse EDTA blood, compared to before horse EDTA blood absorption. If this range of the maximum thickness is retained, the domed section including the cushion section will be resistant to collapse even during periods of wetness after menstrual blood has been absorbed, and the domed section will fit the excretory opening of the wearer, and especially the labia minora, thus reducing leakage.

The reason for dropping 2 g of horse EDTA blood is that the amount of menstrual blood excreted at once by a human is considered to be approximately 2 g. In order to absorb the horse EDTA blood into the cushion section, 2 g of horse EDTA blood is dropped onto the entire cushion section using a pipette, but when the cushion section comprises a water-repellent material, so that the horse EDTA blood is poorly taken up into the cushion section, the horse EDTA blood may be absorbed into the cushion section by applying pressure to the cushion section.

The maximum thickness of the cushion section after absorption of 2 g of horse EDTA blood can be measured at 1 minute after all of the horse EDTA blood has been absorbed. The maximum thickness of the cushion section can also be measured using the aforementioned two-dimensional laser displacement gauge.

The EDTA blood is described below.

In an absorbent article according to one embodiment of the present disclosure, as shown in FIG. 1, the absorbent article has a curved structure in which the domed section curves inward. If the absorbent article has a curved structure, the absorbent article will presumably fit by curving with the body of the wearer, thus further helping to limit leakage of absorbed menstrual blood. The curved structure may be formed, for example, by passing an elastic member such as rubber thread, expanding film or the like through both sides in the lengthwise direction of the absorbent article, and applying tensile force to both sides in the lengthwise direction of the absorbent article.

In an absorbent article according to another embodiment of the present disclosure, the liquid-permeable top sheet has a plurality of ridges and a plurality of furrows on the skin contact surface, extending in the lengthwise direction of the absorbent article (throughout the present specification, the top sheet with a plurality of ridges and a plurality of furrows extending in the lengthwise direction of the absorbent article will sometimes be referred to simply as "top sheet with a ridge-furrow structure"). The top sheet can be produced by the method described in Japanese Unexamined Patent Publication No. 2008-025078, Japanese Unexamined Patent Publication No. 2008-025079, or elsewhere.

For an absorbent article according to yet another embodiment of the present disclosure, the top sheet with a ridge-furrow structure may be produced by the method described in Japanese Unexamined Patent Publication No. 2011-226010, Japanese Unexamined Patent Publication No. 2011-226011, or elsewhere. The top sheet with a ridge-furrow structure can be formed by passing the top sheet to be treated through the gap between a pair of gear rolls with rotational axis lines that are perpendicular to the machine direction, and rotating while a plurality of teeth situated on the peripheral surfaces of each of the gear rolls are mutually engaged, and subjecting it to fluid treatment.

Specifically, the draw ratio of the gear rolls is preferably about 105% or greater, more preferably about 105% to about 500%, even more preferably about 120% to 300%, and even more preferably about 130% to about 200%. If the draw ratio is less than about 105%, the stretchability of the top sheet may be inadequate and the cushion section will more easily collapse during production of the absorbent article, while if the draw ratio is greater than about 500%, the top sheet will tend to tear during production of the absorbent article.

The term "draw ratio" refers to the value calculated by the following formula:

$$\text{Draw ratio (\%)} = 100 \times \left[ \frac{\sqrt{P^2 + 4D^2}}{P} - 1 \right] \qquad \text{[Formula 1]}$$

where P is the gear pitch and D is the gear tooth cutting depth.

In an absorbent article according to yet another embodiment of the present disclosure, the liquid-permeable top sheet has a plurality of slits. If the liquid-permeable top sheet has a plurality of slits running through the top sheet, it will be possible to prevent widening of the slits and excessive collapse of the cushion section during production of the absorbent article. The top sheet with a plurality of slits can be formed by passing the top sheet through a slit roll having longitudinal slits arranged in a zigzag pattern.

The top sheet with a plurality of slits can be produced as described in Japanese Patent Public Inspection No. 2002-528174, for example.

In an absorbent article according to yet another embodiment of the disclosure, the liquid-permeable top sheet has a plurality of open pin holes.

A top sheet having a ridge-furrow structure, slits and open pin holes can prevent excessive collapse of the cushion section during production of the absorbent article, due to change of the shape of the ridge-furrow structure of the top sheet, and opening and closing of the slits and open pin holes. From this viewpoint, the ridge-furrow structure, slits and open pin holes of the top sheet are preferably present at least at the section bordering the cushion section, i.e. the section composing the domed section, but they may also be present over the entire top sheet.

The absorbent article of the present disclosure may have any desired shape such as rectangular, elliptical or gourd-shaped, and it may also have a flap to prevent slipping of clothing such as shorts.

Since the absorbent article of the present disclosure fits with the excretory opening of the wearer and especially the labia minora, helping to prevent leakage, it can be reduced in size, and the absorbent article of the present disclosure may have a length of preferably about 100 to about 500 mm, more preferably about 120 to about 350 mm and even more preferably about 150 to about 250 mm in the lengthwise direction, and a length of preferably about 40 to about 200 mm, more preferably about 45 to about 180 mm and even more preferably about 50 to 100 mm in the widthwise direction.

In the absorbent article of the present disclosure, the absorbent body has a length of preferably about 80 to about 350 mm, more preferably about 100 to 300 mm and even more preferably about 120 to about 250 mm in the lengthwise direction. This is because if a highly-rigid absorbent body has an excessive size in the absorbent article, the domed section will not be able to easily contact the excretory opening, and especially the labia minora. For example, the gluteal region is a region that undergoes very large change during periods when the wearer walks or sits, and when the absorbent body slips at sections bordering the gluteal region, the absorbent body at the sections bordering the excretory opening, and especially the labia minora, is pulled with it and tends to also slip.

In the absorbent article of the present disclosure, the absorbent body has a length of preferably about 30 to about 100 mm, more preferably about 35 to 80 mm and even more preferably about 40 to 70 mm in the widthwise direction. This is because if the width of the absorbent body is excessively greater than the width between the thighs of the wearer, deformation of the absorbent body may lead to diffusion and/or transfer of menstrual blood to other regions, and leakage of the absorbed menstrual blood.

In an absorbent article according to another embodiment of the present disclosure, the domed section comprises a blood modifying agent having an IOB of about 0 to about 0.60, a melting point of no higher than about 45° C., and a water solubility of no greater than about 0.05 g in 100 g of water at 25° C.

The IOB (Inorganic Organic Balance) is an indicator of the hydrophilic-lipophilic balance, and as used herein, it is the value calculated by the following formula by Oda et al.:

IOB=inorganic value/organic value.

The inorganic value and the organic value are based on the organic paradigm described in "Organic compound predictions and organic paradigms" by Fujita A., Kagaku no Ryoiki (Journal of Japanese Chemistry), Vol. 11, No. 10 (1957) p. 719-725.

The organic values and inorganic values of major groups, according to Fujita, are summarized in Table 1 below.

TABLE 1

| Group | Inorganic value | Organic value |
|---|---|---|
| —COOH | 150 | 0 |
| —OH | 100 | 0 |
| —O—CO—O— | 80 | 0 |
| —CO)— | 65 | 0 |
| —COOR | 60 | 0 |
| —O— | 20 | 0 |
| Triple bond | 3 | 0 |
| Double bond | 2 | 0 |
| $CH_2$ | 0 | 20 |
| iso-branch | 0 | −10 |
| tert-branch | 0 | −20 |
| Light metal (salt) | ≥500 | 0 |
| Heavy metal (salt), amine, $NH_3$ salt | ≥400 | 0 |

For example, in the case of an ester of tetradecanoic acid which has 14 carbon atoms and dodecyl alcohol which has 12 carbon atoms, the organic value is 520 ($CH_2$, 20×26) and the inorganic value is 60 (—COOR, 60×1), and therefore IOB=0.12.

In the blood modifying agent, the IOB is about 0-0.60, preferably about 0-0.50, more preferably about 0-0.40 and even more preferably about 0-0.30. This is because a lower IOB is associated with higher organicity and higher affinity with blood cells.

As used herein, the term "melting point" refers to the peak top temperature for the endothermic peak during conversion from solid to liquid, upon measurement with a differential scanning calorimetry analyzer at a temperature-elevating rate of 10° C./min. The melting point may be measured using a Model DSC-60 DSC measuring apparatus by Shimadzu Corp., for example.

If the blood modifying agent has a melting point of no higher than about 45° C., it may be either liquid or solid at room temperature, or in other words, the melting point may be either about 25° C. or higher or below about 25° C., and for example, it may have a melting point of about −5° C. or about −20° C. The reason for a melting point of no higher than about 45° C. for the blood modifying agent will be explained below.

The blood modifying agent does not have a lower limit for the melting point, but the vapor pressure is preferably low. The vapor pressure of the blood modifying agent is preferably no greater than about 0.01 Pa, more preferably no greater than about 0.001 Pa and even more preferably no greater than about 0.0001 Pa, at 1 atmosphere, 25° C. Considering that the absorbent article of this disclosure is to be used in contact with the human body, the vapor pressure is preferably no greater than about 0.01 Pa, more preferably no greater than about 0.001 Pa and even more preferably no greater than about 0.0001 Pa, at 1 atmosphere, 40° C. If the vapor pressure is high, gasification may occur during storage and the amount of blood modifying agent may be reduced, and may create problems such as, odor during wear.

The melting point of the blood modifying agent may also differ depending on the weather or duration of wear. For example, in regions with a mean atmospheric temperature of no higher than about 10° C., using a blood modifying agent with a melting point of no higher than about 10° C. may allow the blood modifying agent to stably modify blood after excretion of menstrual blood, even if it has been cooled by the ambient temperature.

Also, when the absorbent article is used for a prolonged period of time, the melting point of the blood modifying agent is preferably at the high end of the range of no higher than about 45° C. This is because the blood modifying agent is not easily affected by sweat or friction during wearing, and will not easily migrate even during prolonged wearing.

A water solubility of no greater than 0.05 g can be confirmed by adding 0.05 g of sample to 100 g of deionized water at 25° C., allowing the mixture to stand for 24 hours, and gently stirring after 24 hours if necessary and then visually evaluating whether or not the sample has dissolved.

The term "solubility" used herein in regard to water solubility includes cases where the sample completely dissolves in deionized water to form a homogeneous mixture, and cases where the sample is completely emulsified. Here, "completely" means that no mass of the sample remains in the deionized water.

In the art, top sheet surfaces are coated with surfactants in order to alter the surface tension of blood and promote rapid absorption of blood. However, because surfactants generally have high water solubility, the surfactant-coated top sheet is highly miscible with hydrophilic components (such as, blood plasma) in the blood and therefore, instead, they tend to cause residue of blood on the top sheet. The aforementioned blood modifying agent has low water solubility and therefore, unlike conventionally known surfactants, it does not cause residue of blood on the top sheet and allows rapid migration into the absorbent body.

As used herein, a water solubility in 100 g of water at 25° C. may be simply referred to as "water solubility".

The blood modifying agent may have a water solubility of approximately 0 g. Therefore, the lower limit for the water solubility in the blood modifying agent is approximately 0 g.

As used herein, "weight-average molecular weight" includes the concept of a polydisperse compound (for example, a compound produced by stepwise polymerization, an ester formed from a plurality of fatty acids and a plurality of aliphatic monohydric alcohols), and a simple compound (for example, an ester formed from one fatty acid and one aliphatic monohydric alcohol), and in a system comprising $N_i$ molecules with molecular weight $M_i$ (i=1, or i=1, 2 . . . ), it refers to $M_w$ determined by the following formula.

$$M_w = \Sigma N_i M_i^2 / \Sigma N_i M_i$$

As used herein, the weight-average molecular weights are the values measured by gel permeation chromatography (GPC), based on polystyrene.

The GPC measuring conditions may be the following, for example.

Device: Lachrom Elite high-speed liquid chromatogram by Hitachi High-Technologies Corp.
Columns: SHODEX KF-801, KF-803 and KF-804, by Showa Denko K.K.
Eluent: THF
Flow rate: 1.0 mL/min
Driving volume: 100 μL
Detection: RI (differential refractometer)

The weight-average molecular weights listed in the examples of the present specification were measured under the conditions described below.

Examples of the aforementioned blood modifying agents include compounds with the following structures.
(i) Hydrocarbons,
(ii) Compounds having at least one carbonyl bond (—CO—) and/or at least one ether bond (—O—) inserted between a C—C single bond of a hydrocarbon, and
(iii) Compounds having at least one carbonyl bond (—CO—) and/or at least one ether bond (—O—) inserted between a C—C single bond of a hydrocarbon, and having at least one hydrogen on the hydrocarbon substituted with a carboxyl group (—COOH) or hydroxyl group (—OH).

As used herein, "hydrocarbon" refers to a compound composed of carbon and hydrogen, and it may be a chain hydrocarbon, such as, a paraffinic hydrocarbon (containing no double bond or triple bond, also referred to as alkane), an olefin-based hydrocarbon (containing one double bond, also referred to as alkene), an acetylene-based hydrocarbon (containing one triple bond, also referred to as alkyne), or a hydrocarbon comprising two or more bonds selected from the group consisting of double bonds and triple bonds, and cyclic hydrocarbon, such as, aromatic hydrocarbons and alicyclic hydrocarbons.

Preferred as such hydrocarbons are chain hydrocarbons and alicyclic hydrocarbons, with chain hydrocarbons being more preferred, paraffinic hydrocarbons, olefin-based hydrocarbons and hydrocarbons with two or more double bonds (containing no triple bond) being more preferred, and paraffinic hydrocarbons being even more preferred.

Chain hydrocarbons include linear hydrocarbons and branched hydrocarbons.

When two or more ether bonds (—O—) are inserted in the compounds of (ii) and (iii) above, the ether bonds (—O—) are not adjacent each other. Thus, compounds (ii) and (iii) do not include compounds with continuous ether bonds (i.e., peroxides).

In the compounds of (iii), compounds in which at least one hydrogen on the hydrocarbon is substituted with a hydroxyl group (—OH) are preferred over compounds in which at least one hydrogen on the hydrocarbon is substituted with a carboxyl group (—COOH). As shown in Table 1, the carboxyl groups bond with metals and the like in menstrual blood, drastically increasing the inorganic value from 150 to 400 or greater, and therefore a blood modifying agent with carboxyl groups can increase the IOB value to more than about 0.6 during use, potentially lowering the affinity with blood cells.

The blood modifying agent preferably is a compound with one of the following structures.
(i') A hydrocarbon,
(ii') A compound having at least one carbonyl bond (—CO—), at least one ester bond (—COO—), at least one carbonate bond (—OCOO—) and/or at least one ether bond (—O—) inserted between a C—C single bond of a hydrocarbon, or
(iii') A compound having at least one carbonyl bond (—CO—), at least one ester bond (—COO—), at least one carbonate bond (—OCOO—) and/or at least one ether bond (—O—) inserted between a C—C single bond of a hydrocarbon, and having at least one hydrogen on the hydrocarbon substituted with a carboxyl group (—COOH) or hydroxyl group (—OH).

When 2 or more bonds are inserted in the compound of (ii') or (iii'), i.e., when 2 or more bonds selected from among carbonyl bonds (—CO—), ester bonds (—COO—), carbonate bonds (—OCOO—) and ether bonds (—O—) are inserted, the bonds are not adjacent to each other, and at least one carbon atom lies between each of the bonds.

The blood modifying agent is more preferably a compound with no more than about 1.8 carbonyl bonds (—CO—), no more than 2 ester bonds (—COO—), no more than about 1.5 carbonate bonds (—OCOO—), no more than about 6 ether bonds (—O—), no more than about 0.8 carboxyl groups (—COOH) and/or no more than about 1.2 hydroxyl groups (—OH), per 10 carbon atoms in the hydrocarbon.

The blood modifying agent may also be, more preferably,
(A) an ester of a compound with 2-4 hydroxyl groups and a compound with 1 carboxyl group,
(B) an ether of a compound with 2-4 hydroxyl groups and a compound with 1 hydroxyl group,
(C) an ester of a compound with 2-4 carboxyl groups and a compound with 1 hydroxyl group,
(D) a compound having one selected from the group consisting of carbonyl bonds (—CO—), ester bonds (—COO—), carbonate bonds (—OCOO—) and ether bonds (—O—) inserted in a hydrocarbon,
(E) a poly $C_{2-6}$ alkylene glycol, or its ester or ether, or
(F) a chain hydrocarbon.

(A) to (F) will now be described in detail.

[(A) Ester of a Compound with 2-4 Hydroxyl Groups and a Compound with 1 Carboxyl Group]

The ester of a compound with 2-4 hydroxyl groups and a compound with 1 carboxyl group (hereunder also referred to as as "compound (A)") includes esters of a compound with 4, 3 or 2 hydroxyl groups and a compound with 1 carboxyl group, and it is not necessary for all of the hydroxyl groups to be esterified so long as the IOB, melting point and water solubility are within the aforementioned ranges.

Examples of compounds with 2-4 hydroxyl groups include chain hydrocarbon tetraols such as, alkanetetraols, including pentaerythritol, chain hydrocarbon triols such as, alkanetriols, including glycerins, and chain hydrocarbon diols such as alkanediols, including glycols. Examples of compounds with 1 carboxyl group include compounds in which one hydrogen on the hydrocarbon is substituted with one carboxyl group (—COOH), such as fatty acids.

Examples for compound (A) include ($A_1$) esters of chain hydrocarbon tetraols and fatty acids, ($A_2$) esters of chain hydrocarbon triols and fatty acids, and ($A_3$) esters of chain hydrocarbon diols and fatty acids.

[($A_1$) Esters of Chain Hydrocarbon Tetraols and Fatty Acids]

Examples of esters of chain hydrocarbon tetraols and fatty acids include tetraesters of pentaerythritol and fatty acids, represented by the following formula (1):

[Chemical 1]

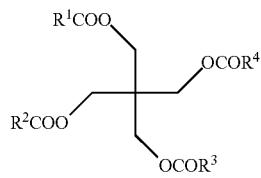

(1)

triesters of pentaerythritol and fatty acids, represented by the following formula (2):

[Chemical 2]

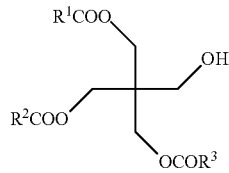

(2)

diesters of pentaerythritol and fatty acids, represented by the following formula (3):

[Chemical 3]

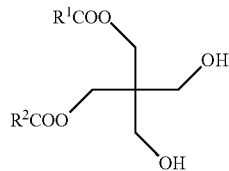

(3)

and monoesters of pentaerythritol and fatty acids, represented by the following formula (4).

[Chemical 4]

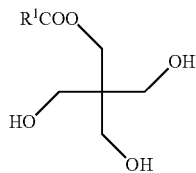

(4)

In the formulas, $R^1$-$R^4$ each represent a chain hydrocarbon.

The fatty acids consisting of the esters of pentaerythritol and fatty acids ($R^1$COOH, $R^2$COOH, $R^3$COOH, and $R^4$COOH) are not particularly restricted so long as the pentaerythritol and fatty acid esters satisfy the conditions for the IOB, melting point and water solubility, and for example, there may be mentioned saturated fatty acids, such as a $C_2$-$C_{30}$ saturated fatty acids, including acetic acid ($C_2$) ($C_2$ representing the number of carbons, corresponding to the number of carbons of $R^1$C, $R^2$C, $R^3$C or $R^4$C, same hereunder), propanoic acid ($C_3$), butanoic acid ($C_4$) and its isomers such as 2-methylpropanoic acid ($C_4$), pentanoic acid ($C_5$) and its isomers such as 2-methylbutanoic acid ($C_5$) and 2,2-dimethylpropanoic acid ($C_5$), hexanoic acid ($C_6$), heptanoic acid ($C_7$), octanoic acid ($C_8$) and its isomers, such as 2-ethylhexanoic acid ($C_8$), nonanoic acid ($C_9$), decanoic acid ($C_{10}$), dodecanoic acid ($C_{12}$), tetradecanoic acid ($C_{14}$), hexadecanoic acid ($C_{16}$), heptadecanoic acid ($C_{17}$), octadecanoic acid ($C_{18}$), eicosanoic acid ($C_{20}$), docosanoic acid ($C_{22}$), tetracosanoic acid ($C_{24}$), hexacosanoic acid ($C_{26}$), octacosanoic acid ($C_{28}$), triacontanoic acid ($C_{30}$), as well as isomers of the foregoing (excluding those mentioned above).

The fatty acid may also be an unsaturated fatty acid. Examples of unsaturated fatty acids include $C_3$-$C_{20}$ unsaturated fatty acids, such as, monounsaturated fatty acids including crotonic acid ($C_4$), myristoleic acid ($C_{14}$), palmitoleic acid ($C_{16}$), oleic acid ($C_{18}$), elaidic acid ($C_{18}$), vaccenic acid ($C_{18}$), gadoleic acid ($C_{20}$) and eicosenoic acid ($C_{20}$), di-unsaturated fatty acids including linolic acid ($C_{18}$) and eicosadienoic acid ($C_{20}$), tri-unsaturated fatty acids including linolenic acids, such as, α-linolenic acid ($C_{18}$) and γ-linolenic acid ($C_{18}$), pinolenic acid ($C_{18}$), eleostearic acids, such as, α-eleostearic acid ($C_{18}$) and β-eleostearic acid ($C_{18}$), Mead acid ($C_{20}$), dihomo-γ-linolenic acid ($C_{20}$) and eicosatrienoic acid ($C_{20}$), tetra-unsaturated fatty acids including stearidonic acid ($C_{20}$), arachidonic acid ($C_{20}$) and eicosatetraenoic acid ($C_{20}$), penta-unsaturated fatty acids including bosseopentaenoic acid ($C_{18}$) and eicosapentaenoic acid ($C_{20}$), and partial hydrogen adducts of the foregoing.

Considering the potential for degradation by oxidation and the like, the ester of pentaerythritol and a fatty acid is preferably an ester of pentaerythritol and a fatty acid, which is derived from a saturated fatty acid, i.e., an ester of pentaerythritol and a saturated fatty acid.

Also, in order to lower the IOB and result in greater hydrophobicity, the ester of pentaerythritol and a fatty acid is preferably a diester, triester or tetraester, more preferably a triester or tetraester, and even more preferably a tetraester.

In a tetraester of pentaerythritol and a fatty acid, the IOB is 0.60 if the total number of carbons of the fatty acid consisting of the tetraester of the pentaerythritol and fatty acid, i.e., the total number of carbons of the $R^1$C, $R^2$C, $R^3$C or $R^4$C portion in formula (1), is 15. Thus, when the total number of carbons in the tetraester of the pentaerythritol and fatty acid is approximately 15 or greater, the IOB satisfies the condition of being within about 0 to 0.6.

Examples of tetraesters of pentaerythritol and fatty acids include tetraesters of pentaerythritol with hexanoic acid ($C_6$), heptanoic acid ($C_7$), octanoic acid ($C_8$) such as, 2-ethylhexanoic acid ($C_8$), nonanoic acid ($C_9$), decanoic acid ($C_{10}$) and/or dodecanoic acid ($C_{12}$).

In a triester of pentaerythritol and a fatty acid, the IOB is 0.58 if the total number of carbons of the fatty acid consisting of the triester of the pentaerythritol and fatty acid, i.e., the total number of carbons of the $R^1C$, $R^2C$ or $R^3C$ portion in formula (2), is 19. Thus, when the total number of carbons of the fatty acid in the triester of the pentaerythritol and fatty acid is approximately 19 or greater, the IOB satisfies the condition of being within about 0 to 0.6.

In a diester of pentaerythritol and a fatty acid, the IOB is 0.59 if the total number of carbons of the fatty acid consisting of the diester of the pentaerythritol and fatty acid, i.e., the total number of carbons of the $R^1C$ or $R^2C$ portion in formula (3), is 22. Thus, when the total number of carbons of the fatty acid in the diester of the pentaerythritol and fatty acid is approximately 22 or greater, the IOB satisfies the condition of being within about 0 to 0.6.

In a monoester of pentaerythritol and a fatty acid, the IOB is 0.60 if the total number of carbons of the fatty acid consisting of the monoester of the pentaerythritol and fatty acid, i.e. the total number of carbons of the $R^1C$ portion in formula (4), is 25. Thus, when the number of carbons of the fatty acid in the monoester of the pentaerythritol and fatty acid is approximately 25 or greater, the IOB satisfies the condition of being within about 0 to 0.6.

The effects of double bonds, triple bonds, iso-branches and tert-branches are not considered in this calculation.

Commercial products which are esters of pentaerythritol and fatty acids include UNISTAR H-408BRS and H-2408BRS-22 (mixed product) (both products of NOF Corp.).

[($A_2$) Esters of Chain Hydrocarbon Triols and Fatty Acids]

Examples of esters of chain hydrocarbon triols and fatty acids include triesters of glycerin and fatty acids, represented by formula (5):

[Chemical 5]

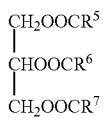

(5)

diesters of glycerin and fatty acids, represented by the following formula (6):

[Chemical 6]

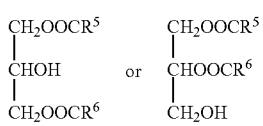

(6)

and monoesters of glycerin and fatty acids, represented by the following formula (7):

[Chemical 7]

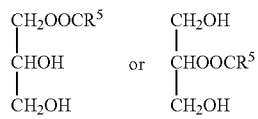

(7)

wherein $R^5$-$R^7$ each represent a chain hydrocarbon.

The fatty acid consisting of the ester of glycerin and a fatty acid ($R^5COOH$, $R^6COOH$ and $R^7COOH$) is not particularly restricted so long as the ester of glycerin and a fatty acid satisfies the conditions for the IOB, melting point and water solubility, and for example, there may be mentioned the fatty acids mentioned for the "($A_1$) Esters of chain hydrocarbon tetraols and fatty acids", namely saturated fatty acids and unsaturated fatty acids, and in consideration of the potential for degradation by oxidation and the like, the ester is preferably a glycerin and fatty acid ester, which is derived from a saturated fatty acid, i.e., an ester of glycerin and a saturated fatty acid.

Also, in order to lower the IOB and result in greater hydrophobicity, the ester of glycerin and a fatty acid is preferably a diester or triester, and more preferably a triester.

A triester of glycerin and a fatty acid is also known as a triglyceride, and examples include triesters of glycerin and octanoic acid ($C_8$), triesters of glycerin and decanoic acid ($C_{10}$), triesters of glycerin and dodecanoic acid ($C_{12}$), triesters of glycerin and 2 or more different fatty acids, and mixtures of the foregoing.

Examples of triesters of glycerin and 2 or more fatty acids include triesters of glycerin with octanoic acid ($C_8$) and decanoic acid ($C_{10}$), triesters of glycerin with octanoic acid ($C_8$), decanoic acid ($C_{10}$) and dodecanoic acid ($C_{12}$), and triesters of glycerin with octanoic acid ($C_8$), decanoic acid ($C_{10}$), dodecanoic acid ($C_{12}$), tetradecanoic acid ($C_{14}$), hexadecanoic acid ($C_{16}$) and octadecanoic acid ($C_{18}$).

In order to obtain a melting point of no higher than about 45° C., preferred triesters of glycerin and fatty acids are those with no more than about 40 as the total number of carbons of the fatty acid consisting of the triester of glycerin and the fatty acid, i.e., the total number of carbons of the $R^5C$, $R^6C$ and $R^7C$ sections in formula (5).

In a triester of glycerin and a fatty acid, the IOB value is 0.60 when the total number of carbons of the fatty acid consisting of the triester of glycerin and the fatty acid, i.e., the total number of carbons of the $R^5C$, $R^6C$ and $R^7C$ sections in formula (5), is 12. Thus, when the total number of carbons of the fatty acid in the triester of the glycerin and fatty acid is approximately 12 or greater, the IOB satisfies the condition of being within about 0 to 0.6.

Triesters of glycerin and fatty acids, being aliphatic and therefore potential constituent components of the human body are preferred from the viewpoint of safety.

Commercial products of triesters of glycerin and fatty acids include tri-coconut fatty acid glycerides, NA36, PANACET 800, PANACET 800B and PANACET 810S, and tri-C2L oil fatty acid glycerides and tri-CL oil fatty acid glycerides (all products of NOF Corp.).

A diester of glycerin and a fatty acid is also known as a diglyceride, and examples include diesters of glycerin and decanoic acid ($C_{10}$), diesters of glycerin and dodecanoic acid ($C_{12}$), diesters of glycerin and hexadecanoic acid ($C_{16}$), diesters of glycerin and 2 or more different fatty acids, and mixtures of the foregoing.

In a diester of glycerin and a fatty acid, the IOB is 0.58 if the total number of carbons of the fatty acid consisting of the diester of the glycerin and fatty acid, i.e., the total number of carbons of the $R^5C$ and $R^6C$ portions in formula (6), is 16. Thus, when the total number of carbons of the fatty acid in the diester of the glycerin and fatty acid is approximately 16 or greater, the IOB satisfies the condition of being about 0 to 0.6.

Monoesters of glycerin and fatty acids are also known as monoglycerides, and examples include glycerin and eicosanoic acid ($C_{20}$) monoester, and glycerin and docosanoic acid ($C_{22}$) monoester.

In a monoester of glycerin and a fatty acid, the IOB is 0.59 if the total number of carbons of the fatty acid consisting of the monoester of the glycerin and fatty acid, i.e. the number of carbons of the $R^5C$ portion in formula (7), is 19. Thus, when the number of carbons of the fatty acid in the monoester of the glycerin and fatty acid is approximately 19 or greater, the IOB satisfies the condition of being about 0 to 0.6.

[($A_3$) Esters of Chain Hydrocarbon Diols and Fatty Acids]

Examples of esters of chain hydrocarbon diols and fatty acids include monoesters and diesters of fatty acids with $C_2$-$C_6$ chain hydrocarbon diols, such as, $C_2$-$C_6$ glycols, including ethylene glycol, propylene glycol, butylene glycol, pentylene glycol and hexylene glycol.

Specifically, examples of esters of chain hydrocarbon diols and fatty acids include diesters of $C_2$-$C_6$ glycols and fatty acids, represented by the following formula (8):

$$R^8COOC_kH_{2k}OCOR^9 \qquad (8)$$

wherein k represents an integer of 2-6, and $R^8$ and $R^9$ each represent a chain hydrocarbon, and monoesters of $C_2$-$C_6$ glycols and fatty acids, represented by the following formula (9):

$$R^8COOC_kH_{2k}OH \qquad (9)$$

wherein k represents an integer of 2-6, and $R^8$ is a chain hydrocarbon.

The fatty acid to be esterified in an ester of a $C_2$-$C_6$ glycol and a fatty acid (corresponding to $R^8COOH$ and $R^9COOH$ in formula (8) and formula (9)) is not particularly restricted so long as the ester of the $C_2$-$C_6$ glycol and fatty acid satisfies the conditions for the IOB, melting point and water solubility, and for example, there may be mentioned the fatty acids mentioned above for the "($A_1$) Esters of chain hydrocarbon tetraols and fatty acids", namely saturated fatty acids and unsaturated fatty acids, and in consideration of the potential for degradation by oxidation and the like, it is preferably a saturated fatty acid.

In a diester of butylene glycol (k=4) and a fatty acid represented by formula (8), IOB is 0.6 when the total number of carbons of the $R^8C$ and $R^9C$ portions is 6. Thus, when the total number of carbon atoms in a diester of butylene glycol (k=4) and a fatty acid represented by formula (8) is approximately 6 or greater, the IOB satisfies the condition of being about 0-0.6. In a monoester of ethylene glycol (k=2) and a fatty acid represented by formula (9), IOB is 0.57 when the total number of carbons of the $R^8C$ portion is 12. Thus, when the total number of carbon atoms in the fatty acid of a monoester of ethylene glycol (k=2) and a fatty acid represented by formula (9) is approximately 12 or greater, the IOB satisfies the condition of being about 0-0.6.

Considering the potential for degradation by oxidation and the like, the ester of the $C_2$-$C_6$ glycol and fatty acid is preferably a $C_2$-$C_6$ glycol and fatty acid ester derived from a saturated fatty acid, or in other words, an ester of a $C_2$-$C_6$ glycol and a saturated fatty acid.

Also, in order to lower the IOB and result in greater hydrophobicity, the ester of the $C_2$-$C_6$ glycol and fatty acid is preferably a glycol and fatty acid ester derived from a glycol with a greater number of carbons, such as an ester of a glycol and a fatty acid derived from butylene glycol, pentylene glycol or hexylene glycol.

Also, in order to lower the IOB and result in greater hydrophobicity, the ester of a $C_2$-$C_6$ glycol and fatty acid is preferably a diester.

Examples of commercial products of esters of $C_2$-$C_6$ glycols and fatty acids include COMPOL BL and COMPOL BS (both products of NOF Corp.).

[(B) Ether of a Compound with 2-4 Hydroxyl Groups and a Compound with 1 Hydroxyl Group]

The ether of a compound with 2-4 hydroxyl groups and a compound with 1 hydroxyl group (hereunder also referred to as "compound (B)") includes ethers of a compound with 4, 3 or 2 hydroxyl groups and a compound with 1 hydroxyl group, and it is not necessary for all of the hydroxyl groups to be etherified so long as the IOB, melting point and water solubility are within the aforementioned ranges.

Compounds with 2-4 hydroxyl groups include those mentioned for "compound (A)", such as, pentaerythritol, glycerin and glycol.

Examples of compounds with 1 hydroxyl group include compounds wherein 1 hydrogen on the hydrocarbon is substituted with 1 hydroxyl group (—OH), such as, aliphatic monohydric alcohols, including saturated aliphatic monohydric alcohols and unsaturated aliphatic monohydric alcohols.

Examples of saturated aliphatic monohydric alcohols include $C_1$-$C_{20}$ saturated aliphatic monohydric alcohols, such as methyl alcohol ($C_1$) ($C_1$ representing the number of carbon atoms, same hereunder), ethyl alcohol ($C_2$), propyl alcohol ($C_3$) and its isomers, including isopropyl alcohol ($C_3$), butyl alcohol ($C_4$) and its isomers, including sec-butyl alcohol ($C_4$) and tert-butyl alcohol ($C_4$), pentyl alcohol ($C_5$), hexyl alcohol ($C_6$), heptyl alcohol ($C_7$), octyl alcohol ($C_8$) and its isomers, including 2-ethylhexyl alcohol ($C_8$), nonyl alcohol ($C_9$), decyl alcohol ($C_{10}$), dodecyl alcohol ($C_{12}$), tetradecyl alcohol ($C_{14}$), hexadecyl alcohol ($C_{16}$), heptadecyl alcohol ($C_{17}$), octadecyl alcohol ($C_{18}$) and eicosyl alcohol ($C_{20}$), as well as their isomers other than those mentioned.

Unsaturated aliphatic monohydric alcohols include those wherein 1 C—C single bond of a saturated aliphatic monohydric alcohol mentioned above is replaced with a C=C double bond, such as oleyl alcohol, and for example, such alcohols are commercially available by New Japan Chemical Co., Ltd. as the RIKACOL Series and UNJECOL Series.

Examples for compound (B) include ($B_1$) ethers of chain hydrocarbon tetraols and aliphatic monohydric alcohols, such as, monoethers, diethers, triethers and tetraethers, preferably diethers, triethers and tetraethers, more preferably triethers and tetraethers and even more preferably tetraethers, ($B_2$) ethers of chain hydrocarbon triols and aliphatic monohydric alcohols, such as, monoethers, diethers and triethers, preferably diethers and triethers and more preferably triethers, and ($B_3$) ethers of chain hydrocarbon diols and aliphatic monohydric alcohols, such as, monoethers and diethers, and preferably diethers.

Examples of ethers of chain hydrocarbon tetraols and aliphatic monohydric alcohols include tetraethers, triethers, diethers and monoethers of pentaerythritol and aliphatic monohydric alcohols, represented by the following formulas (10)-(13):

[Chemical 8]

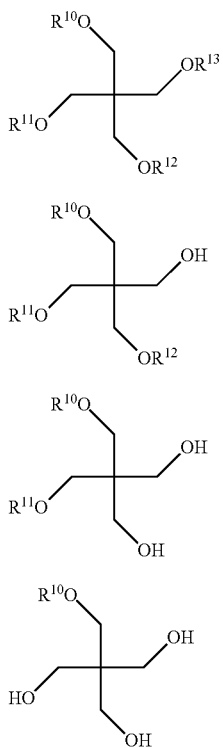

(10)

(11)

(12)

(13)

wherein $R^{10}$-$R^{13}$ each represent a chain hydrocarbon.

Examples of ethers of chain hydrocarbon triols and aliphatic monohydric alcohols include triethers, diethers and monoethers of glycerin and aliphatic monohydric alcohols, represented by the following formulas (14)-(16):

[Chemical 9]

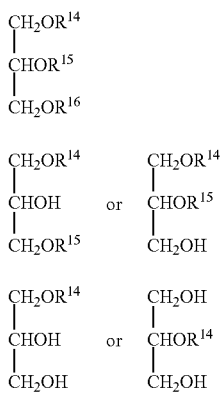

(14)

(15)

(16)

wherein $R^{14}$-$R^{16}$ each represent a chain hydrocarbon.

Ethers of chain hydrocarbon diols and aliphatic monohydric alcohols include diethers of $C_2$-$C_6$ glycols and aliphatic monohydric alcohols, represented by the following formula (17):

$R^{17}OC_nH_{2n}OR^{18}$ (17)

wherein n is an integer of 2-6, and $R^{17}$ and $R^{18}$ are each a chain hydrocarbon, and monoethers of $C_2$-$C_6$ glycols and aliphatic monohydric alcohols, represented by the following formula (18):

$R^{17}OC_nH_{2n}OH$ (18)

wherein n is an integer of 2-6, and $R^{17}$ is a chain hydrocarbon.

In the tetraether of pentaerythritol and an aliphatic monohydric alcohol, the IOB is 0.44 when the total number of carbon atoms of the aliphatic monohydric alcohol consisting of the tetraether of pentaerythritol and the aliphatic monohydric alcohol, i.e., the total number of carbon atoms of the $R^{10}$, $R^{11}$, $R^{12}$ and $R^{13}$ portions in formula (10), is 4. Thus, when the total number of carbon atoms of the aliphatic monohydric alcohol in a tetraether of pentaerythritol and an aliphatic monohydric alcohol is approximately 4 or greater, the IOB value satisfies the condition of being within about 0 to 0.6.

In the triether of pentaerythritol and an aliphatic monohydric alcohol, the IOB is 0.57 when the total number of carbon atoms of the aliphatic monohydric alcohol consisting of the triether of pentaerythritol and the aliphatic monohydric alcohol, i.e., the total number of carbon atoms of the $R^{10}$, $R^{11}$ and $R^{12}$ portions in formula (11), is 9. Thus, when the total number of carbon atoms of the aliphatic monohydric alcohol in a triether of pentaerythritol and an aliphatic monohydric alcohol is approximately 9 or greater, the IOB value satisfies the condition of being within about 0 to 0.6.

In the diether of pentaerythritol and an aliphatic monohydric alcohol, the IOB is 0.60 when the total number of carbon atoms of the aliphatic monohydric alcohol consisting of the diether of pentaerythritol and the aliphatic monohydric alcohol, i.e., the total number of carbon atoms of the $R^{10}$ and $R^{11}$ portions in formula (12), is 15. Thus, when the total number of carbon atoms of the aliphatic monohydric alcohol in a diether of pentaerythritol and an aliphatic monohydric alcohol is approximately 15 or greater, the IOB value satisfies the condition of being within about 0 to 0.6.

In the monoether of pentaerythritol and an aliphatic monohydric alcohol, the IOB is 0.59 when the number of carbon atoms of the aliphatic monohydric alcohol consisting of the monoether of pentaerythritol and the aliphatic monohydric alcohol, i.e. the number of carbon atoms of the $R^{10}$ portion in formula (13), is 22. Thus, when the total number of carbon atoms of the aliphatic monohydric alcohol in a monoether of pentaerythritol and an aliphatic monohydric alcohol is approximately 22 or greater, the IOB value satisfies the condition of being within about 0 to 0.6.

In the triether of glycerin and an aliphatic monohydric alcohol, the IOB is 0.50 when the total number of carbon atoms of the aliphatic monohydric alcohol consisting of the triether of glycerin and the aliphatic monohydric alcohol, i.e., the total number of carbon atoms of the $R^{14}$, $R^{15}$ and $R^{16}$ portions in formula (14), is 3. Thus, when the total number of carbon atoms of the aliphatic monohydric alcohol in a triether of glycerin and an aliphatic monohydric alcohol is approximately 3 or greater, the IOB value satisfies the condition of being within about 0 to 0.6.

In the diether of glycerin and an aliphatic monohydric alcohol, the IOB is 0.58 when the total number of carbon atoms of the aliphatic monohydric alcohol consisting of the diether of glycerin and the aliphatic monohydric alcohol, i.e., the total number of carbon atoms of the $R^{14}$ and $R^{15}$ portions in formula (15), is 9. Thus, when the total number of carbon atoms of the aliphatic monohydric alcohol in a diether of glycerin and an aliphatic monohydric alcohol is approximately 9 or greater, the IOB value satisfies the condition of being within about 0 to 0.6.

In the monoether of glycerin and an aliphatic monohydric alcohol, the IOB is 0.58 when the number of carbon atoms of the aliphatic monohydric alcohol consisting of the monoether of glycerin and the aliphatic monohydric alcohol, i.e., the number of carbon atoms of the $R^{14}$ portion in formula (16), is 16. Thus, when the total number of carbon atoms of the aliphatic monohydric alcohol in a monoether of glycerin and an aliphatic monohydric alcohol is approximately 16 or greater, the IOB value satisfies the condition of being within about 0 to 0.6.

In a diether of butylene glycol (n=4) and aliphatic monohydric alcohol represented by formula (17), the IOB is 0.33 when the total number of carbon atoms of the $R^{17}$ and $R^{18}$ portions is 2. Thus, when the number of carbon atoms of the aliphatic monohydric alcohol in a diether of butylene glycol (n=4) and an aliphatic monohydric alcohol represented by formula (17) is approximately 2 or greater, the IOB value satisfies the condition of being within about 0 to 0.6. Also, in a monoether of ethylene glycol (n=2) and aliphatic monohydric alcohol represented by formula (18), the IOB is 0.60 when the number of carbon atoms of the $R^{17}$ portion is 8. Thus, when the number of carbon atoms of the aliphatic monohydric alcohol in a monoether of ethylene glycol (n=2) and an aliphatic monohydric alcohol represented by formula (18) is approximately 8 or greater, the IOB value satisfies the condition of being within about 0 to 0.6.

Compound (B) may be produced by dehydrating condensation of a compound with 2-4 hydroxyl groups and a compound with 1 hydroxyl group, such as, an aliphatic monohydric alcohol, in the presence of an acid catalyst.

[(C) Ester of a Compound with 2-4 Carboxyl Groups and a Compound with 1 Hydroxyl Group]

The ester of a compound with 2-4 hydroxyl groups and a compound with 1 carboxyl group (hereunder also referred to as "compound (C)") includes esters of a compound with 4, 3 or 2 carboxyl groups and a compound with 1 hydroxyl group, and it is not necessary for all of the carboxyl groups to be esterified so long as the IOB, melting point and water solubility are within the aforementioned ranges.

Examples of compounds with 2-4 carboxyl groups include chain hydrocarbons with 2-4 carboxyl groups, such as, chain hydrocarbon dicarboxylic acids including alkanedicarboxylic acids such as, ethanedioic acid, propanedioic acid, butanedioic acid, pentanedioic acid, hexanedioic acid, heptanedioic acid, octanedioic acid, nonanedioic acid and decanedioic acid, chain hydrocarbon tricarboxylic acids, including alkanetricarboxylic acids such as, propanetrioic acid, butanetrioic acid, pentanetrioic acid, hexanetrioic acid, heptanetrioic acid, octanetrioic acid, nonanetrioic acid and decanetrioic acid, and chain hydrocarbon tetracarboxylic acids, including alkanetetracarboxylic acids such as, butanetetraoic acid, pentanetetraoic acid, hexanetetraoic acid, heptanetetraoic acid, octanetetraoic acid, nonanetetraoic acid and decanetetraoic acid.

Compounds with 2-4 carboxyl groups also include hydroxy acids with 2-4 carboxyl groups, including alkoxy acids with 2-4 carboxyl groups such as, malic acid, tartaric acid, citric acid and isocitric acid, including O-acetylcitric acid, and oxoacids with 2-4 carboxyl groups.

Compounds with 1 hydroxyl group include those mentioned for "compound (B)", such as, aliphatic monohydric alcohols.

Compound (C) may be ($C_1$) an ester, for example a monoester, diester, triester or tetraester, preferably a diester, triester or tetraester, more preferably a triester or tetraester and even more preferably a tetraester, of a chain hydrocarbon tetracarboxylic acid, hydroxy acid, alkoxy acid or oxoacid with 4 carboxyl groups, and an aliphatic monohydric alcohol, ($C_2$) an ester, for example, a monoester, diester or triester, preferably a diester or triester and more preferably a triester, of a chain hydrocarbon tricarboxylic acid, hydroxy acid, alkoxy acid or oxoacid with 3 carboxyl groups, and an aliphatic monohydric alcohol, or ($C_3$) an ester, for example, a monoester or diester, and preferably a diester, of a chain hydrocarbon dicarboxylic acid, hydroxy acid, alkoxy acid or oxoacid with 2 carboxyl groups, and an aliphatic monohydric alcohol.

Examples for compound (C) include dioctyl adipate, and tributyl O-acetylcitrate, of which commercially available products exist.

[(D) Compound Having an Ether Bond (—O—), Carbonyl Bond (—CO—), Ester Bond (—COO—) or Carbonate Bond (—OCOO—) Inserted in a Hydrocarbon]

The compound having a group selected from the group consisting of ether bonds (—O—), carbonyl bonds (—CO—), ester bonds (—COO—) and carbonate bonds (—OCOO—) inserted in a hydrocarbon (hereunder also referred to as "compound (D)") may be ($D_1$) an ether of an aliphatic monohydric alcohol and an aliphatic monohydric alcohol, ($D_2$) a dialkyl ketone, ($D_3$) an ester of a fatty acid and an aliphatic monohydric alcohol, or ($D_4$) a dialkyl carbonate.

[($D_1$) Ether of Aliphatic Monohydric Alcohol and Aliphatic Monohydric Alcohol]

Ethers of aliphatic monohydric alcohols and aliphatic monohydric alcohols include compounds having the following formula (19):

$$R^{19}OR^{20} \qquad (19)$$

wherein $R^{19}$ and $R^{20}$ each represent a chain hydrocarbon.

The aliphatic monohydric alcohol consisting of the ether (corresponding to $R^{19}OH$ and $R^{20}OH$ in formula (19)) is not particularly restricted so long as the ether satisfies the conditions for the IOB, melting point and water solubility, and for example, it may be one of the aliphatic monohydric alcohols mentioned for "compound (B)".

In an ether of an aliphatic monohydric alcohol and an aliphatic monohydric alcohol, the IOB is 0.50 when the total number of carbon atoms of the aliphatic monohydric alcohol consisting of the ether, i.e., the total number of carbons of the $R^{19}$ and $R^{20}$ portions in formula (19), is 2, and therefore when the total number of carbons is about 2 or greater, this condition for the IOB is satisfied. However, with a total number of carbons of about 6, the water solubility is as high as about 2 g, which is problematic from the viewpoint of vapor pressure as well. In order to satisfy the condition of a water solubility of no greater than about 0.05 g, the total number of carbons is preferably about 8 or greater.

[($D_2$) Dialkyl Ketone]

The dialkyl ketone may be a compound of the following formula (20):

$$R^{21}COR^{22} \qquad (20)$$

wherein $R^{21}$ and $R^{22}$ are each an alkyl group.

In a dialkyl ketone, the IOB is 0.54 when the total number of carbon atoms of $R^{21}$ and $R^{22}$ is 5, and therefore this condition for the IOB is satisfied if the total number of carbons is about 5 or greater. However, with a total number of carbons of about 5, the water solubility is as high as about 2 g. Therefore, in order to satisfy the condition of a water solubility of no greater than about 0.05 g, the total number of carbons is preferably about 8 or greater. In consideration of vapor pressure, the number of carbon atoms is preferably about 10 or greater and more preferably about 12 or greater.

If the total number of carbon atoms is about 8, such as in 5-nonanone, for example, the melting point is approximately −50° C. and the vapor pressure is about 230 Pa at 20° C.

The dialkyl ketone may be a commercially available product, or it may be obtained by a known method, such as by oxidation of a secondary alcohol with chromic acid or the like.

[($D_3$) Ester of Fatty Acid and Aliphatic Monohydric Alcohol]

Examples of esters of fatty acids and aliphatic monohydric alcohols include compounds having the following formula (21):

$$R^{23}COOR^{24} \quad (21)$$

wherein $R^{23}$ and $R^{24}$ each represent a chain hydrocarbon.

Examples of fatty acids consisting of these esters (corresponding to $R^{23}COOH$ in formula (21)) include the fatty acids mentioned for the "($A_1$) esters of chain hydrocarbon tetraols and fatty acids", and specifically these include saturated fatty acids and unsaturated fatty acids, with saturated fatty acids being preferred in consideration of the potential for degradation by oxidation and the like. The aliphatic monohydric alcohol consisting of the ester (corresponding to $R^{24}OH$ in formula (21)) may be one of the aliphatic monohydric alcohols mentioned for "compound (B)".

In an ester of such a fatty acid and aliphatic monohydric alcohol, the IOB is 0.60 when the total number of carbon atoms of the fatty acid and aliphatic monohydric alcohol, i.e. the total number of carbon atoms of the $R^{23}C$ and $R^{24}$ portions in formula (21), is 5, and therefore this condition for the IOB is satisfied when the total number of carbon atoms of the $R^{23}C$ and $R^{24}$ portions is about 5 or greater. However, with butyl acetate in which the total number of carbon atoms is 6, the vapor pressure is high at greater than 2,000 Pa. In consideration of vapor pressure, therefore, the total number of carbon atoms is preferably about 12 or greater. If the total number of carbon atoms is about 11 or greater, it will be possible to satisfy the condition of a water solubility of no greater than about 0.05 g.

Examples of esters of such fatty acids and aliphatic monohydric alcohols include esters of dodecanoic acid ($C_{12}$) and dodecyl alcohol ($C_{12}$) and esters of tetradecanoic acid ($C_{14}$) and dodecyl alcohol ($C_{12}$), and examples of commercial products of esters of such fatty acids and aliphatic monohydric alcohols include ELECTOL WE20 and ELECTOL WE40 (both products of NOF Corp.).

[($D_4$) Dialkyl Carbonate]

The dialkyl carbonate may be a compound of the following formula (22):

$$R^{25}OC(=O)OR^{26} \quad (22)$$

wherein $R^{25}$ and $R^{26}$ are each an alkyl group.

In a dialkyl carbonate, the IOB is 0.57 when the total number of carbon atoms of $R^{25}$ and $R^{26}$ is 6, and therefore this condition for the IOB is satisfied if the total number of carbons of $R^{25}$ and $R^{26}$ is about 6 or greater.

In consideration of water solubility, the total number of carbon atoms of $R^{25}$ and $R^{26}$ is preferably about 7 or greater and more preferably about 9 or greater.

The dialkyl carbonate may be a commercially available product, or it may be synthesized by reaction between phosgene and an alcohol, reaction between formic chloride and an alcohol or alcoholate, or reaction between silver carbonate and an alkyl iodide.

[(E) Poly $C_{2-6}$ Alkylene Glycol, or its Ester or Ether]

The poly $C_{2-6}$ alkylene glycol, or its ester or ether (hereunder also referred to as "compound (E)") may be (E a poly $C_{2-6}$ alkylene glycol, ($E_2$) an ester of a poly $C_{2-6}$ alkylene glycol and a fatty acid, ($E_3$) an ether of a poly $C_{2-6}$ alkylene glycol and an aliphatic monohydric alcohol, ($E_4$) an ester of a poly $C_{2-6}$ alkylene glycol and a chain hydrocarbon tetracarboxylic acid, chain hydrocarbon tricarboxylic acid or chain hydrocarbon dicarboxylic acid, or ($E_5$) an ether of a poly $C_{2-6}$ alkylene glycol and a chain hydrocarbon tetraol, chain hydrocarbon triol or chain hydrocarbon diol. These will now be explained.

[($E_1$) Poly $C_{2-6}$ Alkylene Glycol]

Poly $C_{2-6}$ alkylene glycols include not only simple glycol homopolymers but also copolymers and random polymers of 2 or more different glycols. Glycols include $C_{2-6}$ alkylene glycols, such as ethylene glycol, propylene glycol, butylene glycol, pentylene glycol and hexylene glycol. From the viewpoint of lowering the IOB of the poly $C_{2-6}$ alkylene glycol, the glycol is preferably propylene glycol, butylene glycol, pentylene glycol or hexylene glycol, and more preferably butylene glycol, pentylene glycol or hexylene glycol.

As used herein, "poly $C_{2-6}$ alkylene glycol" refers to at least one homopolymer selected from the group consisting of $C_{2-6}$ alkylene glycols, such as ethylene glycol, propylene glycol, butylene glycol, pentylene glycol and hexylene glycol, copolymers of 2 or more selected from the same group, or random polymers of 2 or more selected from the same group.

When the poly $C_{2-6}$ alkylene glycol is a homopolymer, the poly $C_{2-6}$ alkylene glycol is represented by the following formula (23).

$$HO-(C_mH_{2m}O)_n-H \quad (23)$$

The present inventors have confirmed that in polyethylene glycol (corresponding to formula (23) where m=2), when n≥45 (the weight-average molecular weight exceeds about 2,000), the condition for IOB of about 0 to about 0.60 is satisfied, but the condition for the water solubility is not satisfied even when the weight-average molecular weight exceeds about 4,000. Therefore, ethylene glycol homopolymer is not included in the ($E_1$) poly $C_{2-6}$ alkylene glycol, and ethylene glycol should be included in the ($E_1$) poly $C_{2-6}$ alkylene glycol only as a copolymer or random polymer with another glycol.

Thus, homopolymers of formula (23) may include propylene glycol, butylene glycol, pentylene glycol or hexylene glycol homopolymer.

For this reason, m in formula (23) is about 3 to 6 and preferably about 4 to 6, and n is 2 or greater.

The value of n in formula (23) is a value such that the poly $C_{2-6}$ alkylene glycol has an IOB of about 0-0.60, a melting point of no higher than about 45° C. and a water solubility of no greater than about 0.05 g in 100 g of water at 25° C.

For example, when formula (23) is polypropylene glycol (m=3), the IOB is 0.58 when n=12. Thus, when formula (23) is polypropylene glycol (m=3), the condition for the IOB is satisfied when m is equal to or greater than about 12.

Also, when formula (21) is polybutylene glycol (m=4), the IOB is 0.57 when n=7. Thus, when formula (23) is polybutylene glycol (m=4), the condition for the IOB is satisfied when n is equal to or greater than about 7.

From the viewpoint of IOB, melting point and water solubility, the weight-average molecular weight of the poly $C_{4-6}$ alkylene glycol is preferably between about 200 and about 10,000, more preferably between about 250 and about 8,000, and even more preferably in the range of about 250 to about 5,000.

Also from the viewpoint of IOB, melting point and water solubility, the weight-average molecular weight of a poly $C_3$ alkylene glycol, i.e. polypropylene glycol, is preferably between about 1,000 and about 10,000, more preferably between about 3,000 and about 8,000, and even more preferably between about 4,000 and about 5,000. This is because if the weight-average molecular weight is less than about 1,000, the condition for the water solubility will not be satisfied, and a larger weight-average molecular weight will particularly tend to increase the migration rate into the absorbent body and the whiteness of the top sheet.

Examples of commercial products of poly $C_{2-6}$ alkylene glycols include UNIOL™ D-1000, D-1200, D-2000, D-3000, D-4000, PB-500, PB-700, PB-1000 and PB-2000 (all products of NOF Corp.).

[($E_2$) Ester of Poly $C_{2-6}$ Alkylene Glycol and Fatty Acid]

The aforementioned esters of poly $C_{2-6}$ alkylene glycols and fatty acids include the poly $C_{2-6}$ alkylene glycols mentioned for "($E_1$) Poly $C_{2-6}$ alkylene glycol" in which one or both OH ends have been esterified with fatty acids, i.e. monoesters and diesters.

Examples of fatty acids to be esterified in the ester of a poly $C_{2-6}$ alkylene glycol and a fatty acid include the fatty acids mentioned for the "($A_1$) Esters of chain hydrocarbon tetraols and fatty acids", and specifically these include saturated fatty acids and unsaturated fatty acids, with saturated fatty acids being preferred in consideration of the potential for degradation by oxidation and the like.

An example of a commercially available ester of a poly $C_{2-6}$ alkylene glycol and a fatty acid is WILBRITE cp9 (product of NOF Corp.).

[($E_3$) Ether of Poly $C_{2-6}$ Alkylene Glycol and Aliphatic Monohydric Alcohol]

Ethers of such poly $C_{2-6}$ alkylene glycols and aliphatic monohydric alcohols include the poly $C_{2-6}$ alkylene glycols mentioned for "($E_1$) Poly $C_{2-6}$ alkylene glycol" wherein one or both OH ends have been etherified by an aliphatic monohydric alcohol, i.e. monoethers and diethers.

In an ether of a poly $C_{2-6}$ alkylene glycol and an aliphatic monohydric alcohol, the aliphatic monohydric alcohol to be etherified may be an aliphatic monohydric alcohol among those mentioned for "compound (B)".

[($E_4$) Ester of Poly $C_{2-6}$ Alkylene Glycol and Chain Hydrocarbon Tetracarboxylic Acid, Chain Hydrocarbon Tricarboxylic Acid or Chain Hydrocarbon Dicarboxylic Acid]

The poly $C_{2-6}$ alkylene glycol to be esterified for the aforementioned ester of a poly $C_{2-6}$ alkylene glycol and a chain hydrocarbon tetracarboxylic acid, chain hydrocarbon tricarboxylic acid or chain hydrocarbon dicarboxylic acid may be any of the poly $C_{2-6}$ alkylene glycols mentioned above under "($E_1$) Poly $C_{2-6}$ alkylene glycol". Also, the chain hydrocarbon tetracarboxylic acid, chain hydrocarbon tricarboxylic acid or chain hydrocarbon dicarboxylic acid to be esterified may be any of those mentioned above for "compound (C)".

The ester of a poly $C_{2-6}$ alkylene glycol and a chain hydrocarbon tetracarboxylic acid, chain hydrocarbon tricarboxylic acid or chain hydrocarbon dicarboxylic acid may be a commercially available product, or it may be produced by polycondensation of a $C_{2-6}$ alkylene glycol with a chain hydrocarbon tetracarboxylic acid, chain hydrocarbon tricarboxylic acid or chain hydrocarbon dicarboxylic acid under known conditions.

[($E_5$) Ether of Poly $C_{2-6}$ Alkylene Glycol and Chain Hydrocarbon Tetraol, Chain Hydrocarbon Triol or Chain Hydrocarbon Diol]

The poly $C_{2-6}$ alkylene glycol to be etherified for the aforementioned ether of a poly $C_{2-6}$ alkylene glycol and a chain hydrocarbon tetraol, chain hydrocarbon triol or chain hydrocarbon diol may be any of the poly $C_{2-6}$ alkylene glycols mentioned above under "($E_1$) Poly $C_{2-6}$ alkylene glycol". Also, the chain hydrocarbon tetraol, chain hydrocarbon triol or chain hydrocarbon diol to be etherified may be, for example, pentaerythritol, glycerin or glycol, mentioned above for "compound (A)".

Examples of commercially available ethers of poly $C_{2-6}$ alkylene glycols and chain hydrocarbon tetraols, chain hydrocarbon triols and chain hydrocarbon diols include UNILUBE™ 5TP-300 KB and UNIOL™ TG-3000 and TG-4000 (products of NOF Corp.).

UNILUBE™ 5 TP-300 KB is a compound obtained by polycondensation of 65 mol of propylene glycol and 5 mol of ethylene glycol with 1 mol of pentaerythritol, and it has an IOB of 0.39, a melting point of below 45° C., and a water solubility of less than 0.05 g.

UNIOL™ TG-3000 is a compound obtained by polycondensation of 50 mol of propylene glycol with 1 mol of glycerin, and it has an IOB of 0.42, a melting point of below 45° C., a water solubility of less than 0.05 g, and a weight-average molecular weight of about 3,000.

UNIOL™ TG-4000 is a compound obtained by polycondensation of 70 mol of propylene glycol with 1 mol of glycerin, and it has an IOB of 0.40, a melting point of below 45° C., a water solubility of less than 0.05 g, and a weight-average molecular weight of about 4,000.

The ether of a poly $C_{2-6}$ alkylene glycol and a chain hydrocarbon tetraol, chain hydrocarbon triol or chain hydrocarbon diol may also be produced by polycondensation of a $C_{2-6}$ alkylene glycol with a chain hydrocarbon tetraol, chain hydrocarbon triol or chain hydrocarbon diol under known conditions.

[(F) Chain Hydrocarbon]

The chain hydrocarbon has an inorganic value of 0 and thus an IOB of 0, while the water solubility is also approximately 0 g, and therefore if the melting point is no higher than about 45° C. it may be included among the aforementioned blood modifying agents. Examples of such chain hydrocarbons include ($F_1$) chain alkanes, such as straight-chain alkanes and branched chain alkanes, and straight-chain alkanes generally include those with no more than 22 carbons, in consideration of a melting point of no higher than about 45° C. In consideration of vapor pressure, they generally include those with 13 or more carbons. Branched chain alkanes generally include those with 22 or more carbons, since their melting points are often lower than straight-chain alkanes, given the same number of carbon atoms.

Examples of commercially available hydrocarbon products include PARLEAM 6 (NOF Corp.).

The blood modifying agent is believed to have a mechanism of lowering blood viscosity and surface tension, which will be considered in detail in the examples. Menstrual blood to be absorbed by the absorbent article, unlike ordinary blood, contains proteins of the endometrial wall, for example, which act to bind together blood cells so that the blood cells form a rouleau state. Menstrual blood which is to be absorbed by the absorbent article therefore tends to have high viscosity, and when the top sheet is nonwoven fabrics, the menstrual blood becomes clogged between the fibers creating a residual sticky feel for the wearer, while the menstrual blood also diffuses on the surface of the top sheet and tends to leak.

In an embodiment in which the domed section comprises a blood modifying agent which is believed to have a mechanism of lowering blood viscosity and surface tension, it is possible to minimize clogging of menstrual blood between the top sheet fibers and inside the cushion section, and to allow rapid migration of menstrual blood from the top sheet to the absorbent body through the cushion section. In particular, the absorbent article of the present disclosure has the cushion section between the top sheet and the absorbent body in the domed section, and therefore the spacing between the top sheet and the absorbent body tends to be greater than in a conventional absorbent article. Consequently, when the domed section comprises a blood modifying agent, presumably blood that has reached the top sheet can rapidly migrate into the absorbent body through the cushion section, thus further helping to prevent leakage.

In addition, the blood modifying agent which has an IOB of about 0 to 0.60 has high organicity and readily infiltrates between blood cells, and it therefore stabilizes the blood cells and can prevent formation of a rouleau structure by the blood cells.

It is believed that, since the blood modifying agent stabilizes blood cells and helps to prevent formation of a rouleau structure by the blood cells, it facilitates absorption of menstrual blood by the absorbent body. For example, with an absorbent article comprising an acrylic super-absorbent polymer, or SAP, absorption of menstrual blood is known to lead to covering of the SAP surface by rouleau-formed blood cells and inhibition of the absorption performance of the SAP, but presumably stabilization of the blood cells allows the absorption performance of the SAP to be exhibited more easily. In addition, the blood modifying agent which has high affinity with erythrocytes protects the erythrocyte membranes, and therefore may minimize destruction of the erythrocytes.

Any liquid-permeable top sheet that is commonly used in the art may be employed without any particular restrictions, and for example, it may be a sheet-like material having a structure that allows permeation of liquids, such as, a porous film, woven fabric, nonwoven fabric or the like. The fibers composing such a woven fabric or nonwoven fabric may be natural fibers or chemical fibers, with examples of natural fibers including cellulose such as, ground pulp and cotton, and examples of chemical fibers including regenerated cellulose such as, rayon and fibril rayon, semi-synthetic cellulose such as, acetate and triacetate, thermoplastic hydrophobic chemical fibers, and hydrophilicized thermoplastic hydrophobic chemical fibers.

Examples of thermoplastic hydrophobic chemical fibers include polyethylene (PE), polypropylene (PP) and polyethylene terephthalate (PET) monofilaments, and fibers composed of PE and PP graft polymers.

Examples of nonwoven fabrics include air-through nonwoven fabrics, spunbond nonwoven fabrics, point bond nonwoven fabrics, spunlace nonwoven fabrics, needle punching nonwoven fabrics and meltblown nonwoven fabrics, as well as combinations thereof (such as SMS and the like).

Liquid-impermeable back sheets include films comprising PE and PP, air-permeable resin films, air-permeable resin films bonded to spunbond or spunlace nonwoven fabrics, and multilayer nonwoven fabrics such as SMS. In consideration of flexibility of the absorbent article, a low-density polyethylene (LDPE) film with a basis weight of about 15-30 g/m², for example, is preferred.

The first example of the absorbent body is one having an absorbent core covered with a core wrap.

Examples of components for the absorbent core include hydrophilic fibers, including cellulose such as, ground pulp or cotton, regenerated cellulose such as, rayon or fibril rayon, semi-synthetic cellulose such as, acetate or triacetate, particulate polymers, filamentous polymers, thermoplastic hydrophobic chemical fibers, and hydrophilicized thermoplastic hydrophobic chemical fibers, as well as combinations of the foregoing. The component of the absorbent core may also be a super absorbent polymer, such as, granules of a sodium acrylate copolymer or the like.

The core wrap is not particularly restricted so long as it is a substance that is liquid-permeable and with a barrier property that does not allow permeation of the polymer absorber, and it may be a woven fabric or nonwoven fabric, for example. The woven fabric or nonwoven fabric may be made of a natural fiber, chemical fiber, tissue, or the like.

A second example of the absorbent body is one formed from an absorbing sheet or polymer sheet, with a thickness of preferably about 0.3-5.0 mm. The absorbing sheet or polymer sheet may usually be used without any particular restrictions so long as it is one that can be used in an absorbent article such as, a sanitary napkin.

The blood modifying agent may be present at any location in the planar direction of the top sheet, such as, across the entire top sheet, or at the center region near the vaginal opening.

In an embodiment in which the domed section comprises a blood modifying agent, when the liquid-permeable top sheet is formed from a nonwoven fabric or woven fabric, the blood modifying agent preferably does not obstruct the voids between the fibers of the nonwoven fabric or woven fabric, and for example, the blood modifying agent may be attached as droplets or particulates on the surface of the nonwoven fabric fibers, or covering the surfaces of the fibers. On the other hand, in an embodiment in which the domed section comprises a blood modifying agent, when the liquid-permeable top sheet is formed from a porous film, the blood modifying agent preferably does not obstruct the holes in the porous film, and for example, the blood modifying agent may be attached as droplets or particulates on the surface of the porous film. This is because if the blood modifying agent obstructs the voids between the fibers of the nonwoven fabric or woven fabric or the holes in the porous film, migration of the absorbed liquid into the absorbent body may be inhibited.

In an embodiment in which the domed section comprises a blood modifying agent, the blood modifying agent also preferably has a large surface area, in order to allow rapid migration into the absorbed liquid, and a blood modifying agent present as droplets or particulates preferably has a small particle size.

In an embodiment in which the domed section comprises a blood modifying agent, when the material to be coated with the blood modifying agent, such as the top sheet, is a nonwoven fabric or porous film made of a synthetic resin, it is preferably coated with or mixed with a hydrophilic agent for hydrophilicizing treatment. If the original material is hydrophilic, since it is subsequently coated with a lipophilic modifying agent having an IOB of about 0-0.60 and high organicity, there will be created sparsely dispersed lipophilic regions and hydrophilic regions. This presumably allows consistent absorption performance to be exhibited for menstrual blood which consists of hydrophilic components (blood plasma, etc.) and lipophilic components (blood cells, etc.).

In an embodiment in which the domed section comprises a blood modifying agent, there are no particular restrictions on the method of coating the blood modifying agent, and coating may be accomplished with heating as necessary, using a non-contact coater such as, for example, a spiral coater, curtain coater, spray coater or dip coater, or a contact coater or the like. A non-contact coater is preferred from the viewpoint of uniformly dispersing the droplet or particulate modifying agent throughout, and from the viewpoint of not causing damage in the material. The blood modifying agent may be coated directly, if it is a liquid at room temperature, or it may be heated to lower the viscosity, and when it is a solid at room temperature, it may be heated to liquefaction and coated through a control seam HMA gun. By increasing the air pressure of the control seam HMA gun, it is possible to coat the blood modifying agent as fine particulates.

In an embodiment in which the domed section comprises a blood modifying agent, the blood modifying agent may be coated during production of the material for the top sheet and/or second sheet, such as the nonwoven fabric, or it may be coated in the manufacturing line for production of the absorbent article. In an embodiment in which the domed section comprises a blood modifying agent, from the viewpoint of minimizing equipment investment, the blood modifying agent is preferably coated in the manufacturing line for the absorbent article, and in order to prevent shedding of the blood modifying agent which may contaminate the line, the blood modifying agent is preferably coated during a step downstream from the manufacturing line, and specifically, immediately before encapsulation of the product in an individual package.

In an embodiment in which the domed section comprises a blood modifying agent, the blood modifying agent may also have an effect as a lubricant. When the top sheet is a nonwoven fabric, it is possible to reduce friction between fibers, thereby improving the flexibility of the nonwoven fabric as a whole. When the top sheet is a resin film, it is possible to reduce friction between the top sheet and the skin.

In an embodiment in which the domed section comprises a blood modifying agent, the weight-average molecular weight of the blood modifying agent is preferably about 2,000 or less, and more preferably about 1,000 or less. A high weight-average molecular weight will tend to result in high viscosity of the blood modifying agent, and it will be difficult to lower the viscosity of the blood modifying agent by heating, to a viscosity suitable for coating. As a result, it will sometimes be necessary to dilute the blood modifying agent with a solvent. In addition, if the weight-average molecular weight is higher, tack may result in the blood modifying agent itself, tending to create a feeling of unpleasantness for the wearer.

The absorbent article is preferably one intended for absorption of blood, such as a sanitary napkin, panty liner or the like.

EXAMPLES

The disclosure will now be explained by examples, with the understanding that the disclosure is not meant to be limited to the examples.

Production Example 1

As a top sheet there was prepared an air-through nonwoven fabric (basis weight: 30 g/m$^2$) comprising hydrophilicized composite fibers (size: 2.8 dtex) having a core-sheath structure with a polyethylene (PE) sheath and a polyethylene terephthalate (PET) core.

As a cushion section there was prepared an air-through nonwoven fabric (basis weight: 250 g/m$^2$) comprising hydrophilicized composite fibers (size: 2.2 dtex) having a core-sheath structure with a polyethylene (PE) sheath and a polyethylene terephthalate (PET) core. The cushion section before being incorporated into the absorbent article, as shown in FIG. 6(c), had a roughly rounded rectangular shape as the projected form in the thickness direction of the absorbent article, and a constant thickness, while the length in the lengthwise direction was 70 mm, the length in the widthwise direction was 30 mm, and the thickness was 22 mm.

A mixture of pulp and SAP blended at 90:10 (weight ratio) (basis weight: 250 g/m$^2$) was wrapped with tissue (basis weight: 14 g/m$^2$) to form an absorbent body. As a back sheet there was prepared a film comprising PE (basis weight: 23 g/m$^2$), coated with an adhesive on one side.

The absorbent body, cushion section and top sheet were layered in that order, and the absorbent body and top sheet were compressed as shown in FIGS. 1 to 5, to form compressed sections. The outside of the cushion section was compressed, but the cushion section itself was not compressed. Next, the absorbent body and back sheet were bonded and cut as shown in FIGS. 1 to 5, to produce absorbent article No. 1-1. For absorbent article No. 1-1, the length in the lengthwise direction of the domed section was approximately 70 mm, the length in the widthwise direction of the domed section was approximately 35 mm, and the maximum thickness of the cushion section was approximately 10 mm. The length in the lengthwise direction of absorbent article No. 1-1 was approximately 176 mm, and the length in the widthwise direction was approximately 80 mm.

The cushion section had an arched cross-sectional shape as shown in FIG. 3 and FIG. 4, due to tensile force between the compressed top sheet and absorbent body. Thus, in the cushion section, the thickness of the outer peripheral section of the domed section was smaller than the thickness of the center section at the domed section, so that the density of the cushion section at the outer peripheral section of the domed section was clearly higher than the density of the cushion section at the center section of the domed section.

Production Example 2

PANACET 810s (product of NOF Corp., triester of glycerin and fatty acid) was selected as the blood modifying agent, and the PANACET 810s was coated, on the domed section of absorbent article No. 1-1 as the center, from a control seam HMA gun at room temperature, to a basis weight of 5.0 g/m$^2$, to produce absorbent article No. 1-2. With an electron microscope it was confirmed that the PANACET 810s was adhering as fine particulates onto the surfaces of the fibers of the top sheet of the domed section.

Example 1

Absorbent article No. 1-1 was worn by 10 test participants and the responses for a total of 18 tests indicated a low area of surface contamination and low leakage. In addition, the responses indicated that the domed section fit well with the labia minora both during periods of dryness and during periods of wetness.

Also, absorbent article No. 1-2 was worn by several test participants in the same manner, and the responses indicated even lower surface contamination than absorbent article No. 1-1, and no leakage.

Example 2

Additional Blood Modifying Agent Data

A commercially available sanitary napkin was prepared. The sanitary napkin was formed from a top sheet, formed of a hydrophilic agent-treated air-through nonwoven fabric (composite fiber composed of polyester and polyethylene terephthalate, basis weight: 35 g/m$^2$), a second sheet, formed of an air-through nonwoven fabric (composite fiber composed of polyester and polyethylene terephthalate, basis weight: 30 g/m$^2$), an absorbent body comprising pulp (basis weight: 150-450 g/m$^2$, increased at the center section), an acrylic super-absorbent polymer (basis weight: 15 g/m$^2$) and tissue as a core wrap, a water-repellent agent-treated side sheet, and a back sheet composed of a polyethylene film.

The blood modifying agents used for testing are listed below.

[($A_1$) Esters of Chain Hydrocarbon Tetraols and Fatty Acids]
UNISTAR H-408BRS, product of NOF Corp.
Pentaerythritol tetra(2-ethylhexanoate), weight-average molecular weight: approximately 640
UNISTAR H-2408BRS-22, product of NOF Corp.
Mixture of pentaerythritol tetra(2-ethylhexanoate) and neopentylglycol di(2-ethylhexanoate) (58:42 as weight ratio), weight-average molecular weight: approximately 520

[($A_2$) Esters of Chain Hydrocarbon Triols and Fatty Acids]
Cetiol SB45DEO, Cognis Japan
Glycerin and fatty acid triester, with oleic acid or stearylic acid as the fatty acid.
SOY42, product of NOF Corp.
Glycerin and fatty acid triester with $C_{14}$ fatty acid:$C_{16}$ fatty acid:$C_{18}$ fatty acid:$C_{20}$ fatty acid (including both saturated fatty acids and unsaturated fatty acids) at a mass ratio of about 0.2:11:88:0.8, weight-average molecular weight: 880
Tri-C2L oil fatty acid glyceride, product of NOF Corp.
Glycerin and fatty acid triester with $C_8$ fatty acid:$C_{10}$ fatty acid:$C_{12}$ fatty acid at a mass ratio of about 37:7:56, weight-average molecular weight: approximately 570
Tri-CL oil fatty acid glyceride, product of NOF Corp.
Glycerin and fatty acid triester with $C_8$ fatty acid:$C_{12}$ fatty acid at a mass ratio of about 44:56, weight-average molecular weight: approximately 570
PANACET 810s, product of NOF Corp.
Glycerin and fatty acid triester with $C_8$ fatty acid:$C_{10}$ fatty acid at a mass ratio of about 85:15, weight-average molecular weight: approximately 480
PANACET 800, product of NOF Corp.
Glycerin and fatty acid triester with octanoic acid ($C_8$) as the entire fatty acid portion, weight-average molecular weight: approximately 470
PANACET 800B, product of NOF Corp.
Glycerin and fatty acid triester with 2-ethylhexanoic acid ($C_8$) as the entire fatty acid portion, weight-average molecular weight: approximately 470
NA36, product of NOF Corp.
Glycerin and fatty acid triester with $C_{16}$ fatty acid:$C_{18}$ fatty acid:$C_{20}$ fatty acid (including both saturated fatty acids and unsaturated fatty acids) at a mass ratio of about 5:92:3, weight-average molecular weight: approximately 880
Tri-coconut fatty acid glyceride, product of NOF Corp.
Glycerin and fatty acid triester with $C_8$ fatty acid:$C_{10}$ fatty acid:$C_{12}$ fatty acid:$C_{14}$ fatty acid:$C_{16}$ fatty acid (including both saturated fatty acids and unsaturated fatty acids) at a mass ratio of about 4:8:60:25:3, weight-average molecular weight: 670
Caprylic acid diglyceride, product of NOF Corp.
Glycerin and fatty acid diester with octanoic acid as the fatty acid, weight-average molecular weight: approximately 340

[($A_3$) Esters of Chain Hydrocarbon Diols and Fatty Acids]
COMPOL BL, product of NOF Corp.
Dodecanoic acid ($C_{12}$) monoester of butylene glycol, weight-average molecular weight: approximately 270
COMPOL BS, product of NOF Corp.
Octadecanoic acid ($C_{18}$) monoester of butylene glycol, weight-average molecular weight: approximately 350
UNISTAR H-208BRS, product of NOF Corp.
Neopentyl glycol di(2-ethylhexanoate), weight-average molecular weight: approximately 360

[($C_2$) Ester of Chain Hydrocarbon Tricarboxylic Acid, Hydroxy Acid, Alkoxy Acid or Oxoacid with 3 Carboxyl Groups, and Aliphatic Monohydric Alcohol]
Tributyl 0-acetylcitrate, product of Tokyo Kasei Kogyo Co., Ltd.
Weight-average molecular weight: approximately 400

[($C_3$) Ester of Chain Hydrocarbon Dicarboxylic Acid, Hydroxy Acid, Alkoxy Acid or Oxoacid with 2 Carboxyl Groups, and Aliphatic Monohydric Alcohol]
Dioctyl adipate, product of Wako Pure Chemical Industries, Ltd.
Weight-average molecular weight: approximately 380

[($D_3$) Esters of Fatty Acid and Aliphatic Monohydric Alcohol]
ELECTOL WE20, product of NOF Corp.
Ester of dodecanoic acid ($C_{12}$) and dodecyl alcohol ($C_{12}$), weight-average molecular weight: approximately 360
ELECTOL WE40, product of NOF Corp.
Ester of tetradecanoic acid ($C_{14}$) and dodecyl alcohol ($C_{12}$), weight-average molecular weight: approximately 390

[($E_1$) Poly $C_{2-6}$ Alkylene Glycols]
UNIOL D-1000, product of NOF Corp.
Polypropylene glycol, weight-average molecular weight: approximately 1,000
UNIOL D-1200, product of NOF Corp.
Polypropylene glycol, weight-average molecular weight: approximately 1,200
UNIOL D-3000, product of NOF Corp.
Polypropylene glycol, weight-average molecular weight: approximately 3,000
UNIOL D-4000, product of NOF Corp.
Polypropylene glycol, weight-average molecular weight: approximately 4,000
UNIOL PB500, product of NOF Corp.
Polybutylene glycol, weight-average molecular weight: approximately 500
UNIOL PB700, product of NOF Corp.
Polyoxybutylene polyoxypropylene glycol, weight-average molecular weight: approximately 700
UNIOL PB1000R, product of NOF Corp.
Polybutylene glycol, weight-average molecular weight: approximately 1000

[($E_2$) Ester of Poly $C_{2-6}$ Alkylene Glycol and Fatty Acid]
WILBRITE cp9, product of NOF Corp.
Polybutylene glycol compound with OH groups at both ends esterified by hexadecanoic acid ($C_{16}$), weight-average molecular weight: approximately 1,150

[(E₃) Ether of Poly C$_{2-6}$ Alkylene Glycol and Fatty Acid]

UNILUBE MS-70K, product of NOF Corp.

Stearyl ether of polypropylene glycol, approximately 15 repeating units, weight-average molecular weight: approximately 1,140

[(E₅) Ethers of Poly C$_{2-6}$ Alkylene Glycol and Chain Hydrocarbon Tetraol, Chain Hydrocarbon Triol or Chain Hydrocarbon Diol]

UNILUBE 5TP-300 KB

Polyoxyethylenepolyoxypropylene pentaerythritol ether, produced by addition of 5 mol of ethylene oxide and 65 mol of propylene oxide to 1 mol of pentaerythritol, weight-average molecular weight: 4,130

UNIOL TG-3000, product of NOF Corp.

Glyceryl ether of polypropylene glycol, approximately 16 repeating units, weight-average molecular weight: approximately 3,000

UNIOL TG-4000, product of NOF Corp.

Glyceryl ether of polypropylene glycol, approximately 16 repeating units, weight-average molecular weight: approximately 4,000

[(F₁) Chain Alkane]

PARLEAM 6, product of NOF Corp.

Branched chain hydrocarbon, produced by copolymerization of liquid isoparaffin, isobutene and n-butene followed by hydrogen addition, polymerization degree: approximately 5-10, weight-average molecular weight: approximately 330

[Other Materials]

NA50, product of NOF Corp.

Glycerin and fatty acid triester obtained by addition of hydrogen to NA36 for reduced proportion of double bonds from unsaturated fatty acid starting material, weight-average molecular weight: approximately 880

(Caprylic acid/capric acid) monoglyceride, product of NOF Corp.

Glycerin and fatty acid monoester, with octanoic acid (C₈) and decanoic acid (C₁₀) at a mass ratio of about 85:15, weight-average molecular weight: approximately 220

Monomuls 90-L2 lauric acid monoglyceride, product of Cognis Japan

Isopropyl citrate, product of Tokyo Kasei Kogyo Co., Ltd.

Weight-average molecular weight: approximately 230

Diisostearyl malate

Weight-average molecular weight: approximately 640

UNIOL D-400, product of NOF Corp.

Polypropylene glycol, weight-average molecular weight: approximately 400

PEG1500, product of NOF Corp.

Polyethylene glycol, weight-average molecular weight: approximately 1,500-1,600

NONION S-6, product of NOF Corp.

Polyoxyethylene monostearate, approximately 7 repeating units, weight-average molecular weight: approximately 880

WILBRITE s753, product of NOF Corp.

Polyoxyethylene polyoxypropylene polyoxybutylene glycerin, weight-average molecular weight: approximately 960

UNIOL TG-330, product of NOF Corp.

Glyceryl ether of polypropylene glycol, approximately 6 repeating units, weight-average molecular weight: approximately 330

UNIOL TG-1000, product of NOF Corp.

Glyceryl ether of polypropylene glycol, approximately 16 repeating units, weight-average molecular weight: approximately 1,000

UNILUBE DGP-700, product of NOF Corp.

Diglyceryl ether of polypropylene glycol, approximately 9 repeating units, weight-average molecular weight: approximately 700

UNIOX HC60, product of NOF Corp.

Polyoxyethylene hydrogenated castor oil, weight-average molecular weight: approximately 3,570

Vaseline, product of Cognis Japan

Petroleum-derived hydrocarbon, semi-solid

The IOBs, melting points and water solubilities of the samples are shown in Table 2.

The water solubility was measured by the method described above, and samples that dissolved 24 hours after addition of 20.0 g to 100 g of desalted water were evaluated as "20 g<", and samples of which 0.05 g dissolved in 100 g of desalted water but 1.00 g did not dissolve were evaluated as 0.05-1.00 g.

For the melting point, "<45" indicates a melting point of below 45° C.

The skin contact surface of the top sheet of the sanitary napkin was coated with the aforementioned blood modifying agent. Each blood modifying agent was used directly, when the blood modifying agent was liquid at room temperature, or when the blood modifying agent was solid at room temperature it was heated to its melting point+20° C., and a control seam HMA gun was used for atomization of the blood modifying agent and coating onto the entire skin contact surface of the top sheet to a basis weight of about 5 g/m².

Figure 7:
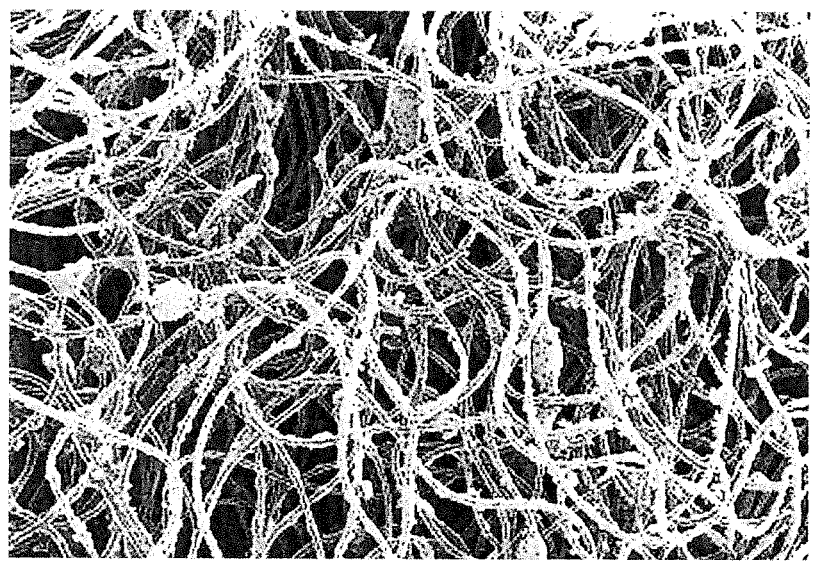
FIG. 7 is an electron micrograph of the skin contact surface of a top sheet in a sanitary napkin wherein the top sheet comprises tri-C2L oil fatty acid glycerides.

FIG. 7 is an electron micrograph of the skin contact surface of a top sheet in a sanitary napkin (No. 2-5) wherein the top sheet comprises tri-C2L oil fatty acid glycerides. As clearly seen in FIG. 7, the tri-C2L oil fatty acid glycerides are adhering onto the fiber surfaces as fine particulates.

The rewetting rate and absorbent body migration rate were measured by the procedure described above. The results are shown in Table 2 below.

Next, the whiteness of the skin contact surface of the top sheet after the absorbent body migration rate test was visually evaluated on the following scale.

VG (Very Good): Virtually no redness of blood remaining, and no clear delineation between areas with and without blood.

G (Good): Slight redness of blood remaining, but difficult to delineate between areas with and without blood.

F (Fair): Slight redness of blood remaining, areas with blood discernible.

P (Poor): Redness of blood completely remaining.

The results are summarized in Table 2.

TABLE 2

| No. | Type | Blood modifying agent Product name | IOB | Melting pt. (° C.) | Water solubility (g) | Weight-average mol. wt. | Rewetting rate (%) | Absorbent body migration rate (sec) | Top sheet whiteness |
|---|---|---|---|---|---|---|---|---|---|
| 2-1 | (A$_1$) | H-408BRS | 0.13 | <−5 | <0.05 | 640 | 1.2 | 3 | VG |
| 2-2 | | H-2408BRS-22 | 0.18 | <−5 | <0.05 | 520 | 2.0 | 3 | VG |
| 2-3 | (A$_2$) | Cetiol SB45DEO | 0.16 | 44 | <0.05 | | 7.0 | 6 | VG |
| 2-4 | | SOY42 | 0.16 | 43 | <0.05 | 880 | 5.8 | 8 | VG |
| 2-5 | | Tri C2L oil fatty acid glyceride | 0.27 | 37 | <0.05 | 570 | 0.3 | 3 | VG |
| 2-6 | | Tri CL oil fatty acid glyceride | 0.28 | 38 | <0.05 | 570 | 1.7 | 3 | VG |
| 2-7 | | PANACET 810s | 0.32 | −5 | <0.05 | 480 | 2.8 | 3 | VG |
| 2-8 | | PANACET 800 | 0.33 | −5 | <0.05 | 470 | 0.3 | 3 | VG |
| 2-9 | | PANACET 800B | 0.33 | −5 | <0.05 | 470 | 2.0 | 3 | VG |
| 2-10 | | NA36 | 0.16 | 37 | <0.05 | 880 | 3.9 | 5 | VG |
| 2-11 | | Tri-coconut fatty acid glyceride | 0.28 | 30 | <0.05 | 670 | 4.3 | 5 | VG |
| 2-12 | | Caprylic diglyceride | 0.58 | <45 | <0.05 | 340 | 4.2 | 9 | G |
| 2-13 | (A$_3$) | COMPOL BL | 0.50 | 2 | <0.05 | 270 | 2.0 | 5 | G |
| 2-14 | | COMPOL BS | 0.36 | 37 | <0.05 | 350 | 7.9 | 9 | G |
| 2-15 | | H-208BRS | 0.24 | <−5 | <0.05 | 360 | 2.0 | 5 | VG |
| 2-16 | (C$_2$) | Tributyl O-acetylcitrate | 0.60 | <45 | <0.05 | 400 | 6.2 | 8 | VG |
| 2-17 | (C$_3$) | Dioctyl adipate | 0.27 | <45 | <0.05 | 380 | 1.7 | 6 | VG |
| 2-18 | (D$_3$) | ELECTOL WE20 | 0.13 | 29 | <0.05 | 360 | 1.8 | 5 | VG |
| 2-19 | | ELECTOL WE40 | 0.12 | 37 | <0.05 | 390 | 1.8 | 4 | VG |
| 2-20 | (E$_1$) | UNIOL D-1000 | 0.51 | <45 | <0.05 | 1,000 | 6.8 | 15 | g0 |
| 2-21 | | UNIOL D-1200 | 0.48 | <45 | <0.05 | 1,160 | 0.5 | 11 | g0 |
| 2-22 | | UNIOL D-3000 | 0.39 | <45 | <0.05 | 3,000 | 1.7 | 10 | g0 |
| 2-23 | | UNIOL D-4000 | 0.38 | <45 | <0.05 | 4,000 | 1.0 | 7 | G |
| 2-24 | (E$_1$) | UNIOL PB500 | 0.44 | <45 | <0.05 | 500 | 4.5 | 4 | G |
| 2-25 | | UNIOL PB700 | 0.49 | −5 | <0.05 | 700 | 2.8 | 5 | G |
| 2-26 | | UNIOL PB1000R | 0.40 | <45 | <0.05 | 1,000 | 4.0 | 4 | G |
| 2-27 | (E$_2$) | WILBRITE cp9 | 0.21 | 35 | <0.05 | 1,150 | 1.4 | 3 | G |
| 2-28 | (E$_3$) | UNILUBE MS-70K | 0.30 | <−10 | <0.05 | 1,140 | 6.7 | 3 | G |
| 2-29 | (E$_5$) | UNILUBE 5TP-300KB | 0.39 | <45 | <0.05 | 4,130 | 2.0 | 6 | G |
| 2-30 | | UNIOL TG-3000 | 0.42 | <45 | <0.05 | 3,000 | 0.8 | 6 | G |
| 2-31 | | UNIOL TG-4000 | 0.40 | <45 | <0.05 | 4,000 | 2.0 | 6 | G |
| 2-32 | (F$_1$) | PARLEAM 6 | 0.00 | −5 | <0.05 | 330 | 6.0 | 8 | VG |
| 2-33 | | NA50 | 0.18 | 52 | <0.05 | 880 | 15.5 | 60 | P |
| 2-34 | | (Caprylic/capric) monoglyceride | 1.15 | <45 | 20< | 220 | 4.0 | 4 | P |
| 2-35 | | 90-L2 Lauric acid monoglyceride | 0.87 | 58 | 20< | | 6.2 | 7 | P |
| 2-36 | | Isopropyl citrate | 1.56 | <45 | 20< | 230 | 12.2 | 5 | G |
| 2-37 | | Diisostearyl malate | 0.28 | <45 | 20< | 640 | 5.5 | 8 | g0 |
| 2-38 | | UNIOL D-400 | 0.76 | <45 | 0.05< | 400 | 8.7 | 40 | P |
| 2-39 | | PEG1500 | 0.78 | 40 | 20< | 1,500-1,600 | 11.0 | 38 | P |
| 2-40 | | NONION S-6 | 0.44 | 37 | 0.05< | 880 | 8.4 | 7 | P |
| 2-41 | | WILBRITE s7- | 0.67 | −5 | 20< | 960 | 9.3 | 9 | g0 |
| 2-42 | | UNIOL TG-330 | 1.27 | <45 | 0.05< | 330 | — | — | — |
| 2-43 | | UNIOL TG-1000 | 0.61 | <45 | <0.05 | 1,000 | 14.2 | 7 | G |
| 2-44 | | UNIOL DGP-700 | 0.90 | <0 | 0.05< | 700 | — | — | — |
| 2-45 | | UNIOX HC60 | 0.46 | 33 | 0.05-1.00 | 3,570 | 14.6 | 46 | P |
| 2-46 | | Vaseline | 0.00 | 55 | <0.05 | | 9.7 | 10 | g0 |
| 2-47 | | None | — | — | — | — | 22.7 | 60< | P |

In the absence of a blood modifying agent, the rewetting rate was 22.7% and the absorbent body migration rate was greater than 60 seconds, but the glycerin and fatty acid triesters all produced rewetting rates of no greater than 7.0% and absorbent body migration rates of no longer than 8 seconds, and therefore significantly improved the absorption performance. Of the glycerin and fatty acid triesters, however, no great improvement in absorption performance was seen with NA50 which had a melting point of above 45° C.

Similarly, the absorption performance was also significantly improved with blood modifying agents having an IOB of about 0-0.60, a melting point of no higher than about 45° C., and a water solubility of no greater than about 0.05 g in 100 g of water at 25° C.

Next, several volunteer subjects were asked to wear sanitary napkins Nos. 2-1 to 2-47, and the obtained responses indicated that with the sanitary napkins comprising blood modifying agents Nos. 2-1 to 2-32, the top sheets had no sticky feel and the top sheets were smooth, even after absorption of menstrual blood.

Also, with sanitary napkins No. 2-1 to No. 2-32, and particularly with sanitary napkins that comprised blood modifying agents Nos. 2-1 to 11, 15 to 19 and 32, the skin contact surfaces of the top sheets after absorption of menstrual blood had not been reddened by the blood and the unpleasantness was minimal.

Example 2 is an example in which the sanitary napkin did not have the prescribed domed section, and since sanitary napkins No. 2-1 to No. 2-32 had the same results as No. 2-7 which contained PANACET 810s, this suggests that the same result would be obtained as with absorbent article No. 1-2, if the blood modifying agents used in sanitary napkins No. 2-1 to No. 2-32 are coated onto absorbent article No. 1-1 produced in Example 1.

Example 3

The rewetting rate was evaluated for blood from different animals, by the procedure described above. The following blood was used for the test.

[Animal Species]
(1) Human
(2) Horse
(3) Sheep

[Types of Blood]

Defibrinated blood: blood sampled and agitated together with glass beads in an Erlenmeyer flask for approximately 5 minutes.

EDTA blood: 65 mL of venous blood with addition of 0.5 mL of a 12% EDTA·2K isotonic sodium chloride solution.

[Fractionation]

Serum or blood plasma: Supernatant obtained after centrifugation of defibrinated blood or EDTA blood for 10 minutes at room temperature at about 1900 G.

Blood cells: Obtained by removing the serum from the blood, washing twice with phosphate buffered saline (PBS), and adding phosphate buffered saline to the removed serum portion.

An absorbent article was produced in the same manner as Example 2, except that the tri-C2L oil fatty acid glyceride was coated at a basis weight of about 5 g/m$^2$, and the rewetting rate of each of the aforementioned blood samples was evaluated. Measurement was performed 3 times for each blood sample, and the average value was recorded.

The results are shown in Table 3 below.

TABLE 3

| | | | Rewetting rate (%) | |
|---|---|---|---|---|
| No. | Animal species | Type of blood | With blood modifying agent | Without blood modifying agent |
| 1 | Human | Defibrinated blood | 1.6 | 5.0 |
| 2 | | Defibrinated serum | 0.2 | 2.6 |
| 3 | | Defibrinated blood cells | 0.2 | 1.8 |
| 4 | | EDTA blood | 2.6 | 10.4 |
| 5 | | EDTA plasma | 0.0 | 5.8 |
| 6 | | EDTA blood cells | 0.2 | 4.3 |
| 7 | Horse | Defibrinated blood | 0.0 | 8.6 |
| 8 | | Defibrinated serum | 0.2 | 4.2 |
| 9 | | Defibrinated blood cells | 0.2 | 1.0 |
| 10 | | EDTA blood | 6.0 | 15.7 |
| 11 | | EDTA plasma | 0.1 | 9.0 |
| 12 | | EDTA blood cells | 0.1 | 1.8 |
| 13 | Sheep | Defibrinated blood | 0.2 | 5.4 |
| 14 | | Defibrinated serum | 0.3 | 1.2 |
| 15 | | Defibrinated blood cells | 0.1 | 1.1 |
| 16 | | EDTA blood | 2.9 | 8.9 |
| 17 | | EDTA plasma | 0.0 | 4.9 |
| 18 | | EDTA blood cells | 0.2 | 1.6 |

The same trend was seen with human and sheep blood as with the horse EDTA blood, as obtained in Example 2. A similar trend was also observed with defibrinated blood and EDTA blood.

Example 4

Evaluation of Blood Retention

The blood retention was evaluated for a top sheet comprising a blood modifying agent and a top sheet comprising no blood modifying agent.

[Test Methods]

(1) A tri-C2L oil fatty acid glyceride was atomized on the skin contact surface of a top sheet formed from an air-through nonwoven fabric (composite fiber composed of polyester and polyethylene terephthalate, basis weight: 35 g/m$^2$), using a control seam HMA gun, for coating to a basis weight of about 5 g/m$^2$. For comparison, there was also prepared a sheet without coating with the tri-C2L oil fatty acid glyceride. Next, both the tri-C2L oil fatty acid glyceride-coated top sheet and the non-coated top sheet were cut to a size of 0.2 g, and the mass (a) of the cell strainer+ top sheet was precisely measured.

(2) After adding about 2 mL of horse EDTA blood from the skin contact surface side, it was allowed to stand for 1 minute.

(3) The cell strainer was set in a centrifuge tube, and subjected to spin-down to remove the excess horse EDTA blood.

(4) The mass (b) of the top sheet containing the cell strainer+ horse EDTA blood was measured.

(5) The initial absorption (g) per 1 g of top sheet was calculated by the following formula.

Initial absorption=[mass($b$)−mass($a$)]/0.2

(6) The cell strainer was again set in the centrifuge tube and centrifuged at room temperature for 1 minute at approximately 1,200 G.

(7) The mass (c) of the top sheet containing the cell strainer+ horse EDTA blood was measured.

(8) The post-test absorption (g) per 1 g of top sheet was calculated by the following formula.

Post-test absorption=[mass($c$)−mass($a$)]/0.2

(9) The blood retention (%) was calculated according to the following formula.

Blood retention (%)=100×post-test absorption/initial absorption

The measurement was conducted 3 times, and the average value was recorded.

The results are shown in Table 4 below.

TABLE 4

| | Blood retention (%) | |
|---|---|---|
| | With blood modifying agent | Without blood modifying agent |
| Horse EDTA blood | 3.3 | 9.2 |

The top sheets comprising blood modifying agents had low blood retentions, suggesting that blood rapidly migrated into the absorbent body after absorption.

Example 5

Viscosity of Blood Containing Blood Modifying Agent

The viscosity of the blood modifying agent-containing blood was measured using a Rheometric Expansion System ARES (Rheometric Scientific, Inc.). After adding 2 mass % of PANACET 810s to horse defibrinated blood, the mixture was gently agitated to form a sample, the sample was placed on a 50 mm-diameter parallel plate, with a gap of 100 µm, and the viscosity was measured at 37±0.5° C. The sample was not subjected to a uniform shear rate due to the parallel plate, but the average shear rate indicated by the device was 10 s$^{-1}$.

The viscosity of the horse defibrinated blood containing 2 mass % PANACET 810s was 5.9 mPa·s, while the viscosity of the horse defibrinated blood containing no blood modifying agent was 50.4 mPa·s. Thus, the horse defibrinated blood containing 2 mass % PANACET 810s clearly had an approximately 90% lower viscosity than the blood containing no blood modifying agent.

It is known that blood contains components such as, blood cells and has thixotropy, and it is believed that the blood modifying agent of this disclosure can lower blood viscosity in the low viscosity range. Lowering the blood viscosity presumably allows absorbed menstrual blood to rapidly migrate from the top sheet to the absorbent body.

Example 6

Photomicrograph of Blood Modifying Agent-Containing Blood

Menstrual blood was sampled from healthy volunteers onto Saran Wrap™, and PANACET 810s dispersed in a 10-fold mass of phosphate-buffered saline was added to a portion thereof to a PANACET 810s concentration of 1 mass %. The menstrual blood was dropped onto a slide glass, a cover glass was placed thereover, and the state of the erythrocytes was observed with an optical microscope. A photomicrograph of menstrual blood containing no blood modifying agent is shown in FIG. 8(a), and a photomicrograph of menstrual blood containing PANACET 810s is shown in FIG. 8(b).

From FIG. 7 it is seen that the erythrocytes formed aggregates such as, rouleaux in the menstrual blood containing no blood modifying agent, while the erythrocytes were stably dispersed in the menstrual blood containing PANACET 810s. This suggests that the blood modifying agent functions to stabilize erythrocytes in blood.

Example 7

Surface Tension of Blood Containing Blood Modifying Agent

The surface tension of blood containing a blood modifying agent was measured by the pendant drop method, using a Drop Master500 contact angle meter by Kyowa Interface Science Co., Ltd. The surface tension was measured after adding a prescribed amount of blood modifying agent to sheep defibrinated blood, and thoroughly shaking.

Figure 9:
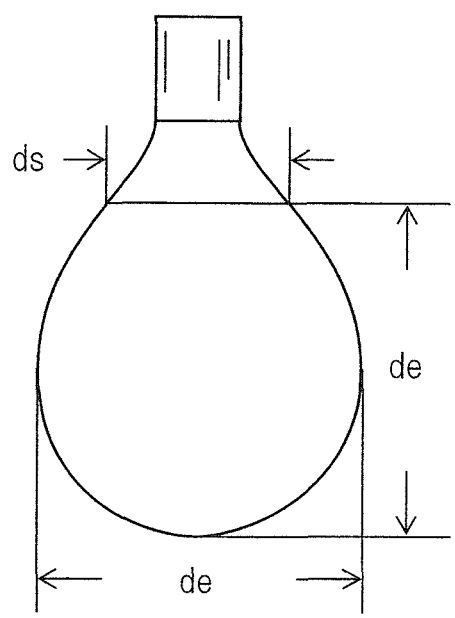
FIG. 9 is a diagram illustrating a method of measuring surface tension.

The measurement was accomplished automatically with a device, and the density γ was determined by the following formula (see FIG. 9B).

$\gamma = g \times \rho \times (de)^2 \times 1/H$ g: Gravitational constant
1/H: Correction factor determined from ds/de
ρ: Density
de: Maximum diameter
ds: Diameter at location of increase by de from dropping edge The density ρ was measured at the temperatures listed in Table 5, according to JIS K 2249-1995, "Density test methods and density/mass/volume conversion tables", "5. Vibrating density test method".

The measurement was accomplished using a DA-505 by Kyoto Electronics Co., Ltd.

The results are shown in Table 5 below.

TABLE 5

| No. | Blood modifying agent Type | Amount (mass %) | Measuring temperature (° C.) | Surface tension (mN/m) |
|---|---|---|---|---|
| 1 | — | — | 35 | 62.1 |
| 2 | PANACET | 0.01 | 35 | 61.5 |
| 3 | 810s | 0.05 | 35 | 58.2 |
| 4 | | 0.10 | 35 | 51.2 |
| 5 | ELECTOL WE20 | 0.10 | 35 | 58.8 |
| 6 | PARLEAM 6 | 0.10 | 35 | 57.5 |
| 7 | — | — | 50 | 56.3 |
| 8 | WILBRITE cp9 | 0.10 | 50 | 49.1 |

Table 5 shows that the blood modifying agent can lower the surface tension of blood despite its very low solubility in water, as seen by a water solubility of no greater than 0.05 g in 100 g of water at 25° C.

Lowering the surface tension of blood presumably allows absorbed blood to rapidly migrate from the top sheet to the absorbent body, without being retained between the top sheet fibers.

The present disclosure relates to the following J1 to J15.

[J1]

An absorbent article comprising a liquid-permeable top sheet, a liquid-impermeable back sheet and an absorbent body between the liquid-permeable top sheet and liquid-impermeable back sheet, wherein the absorbent article has in the excretory opening contact region a domed section that protrudes in the thickness direction of the absorbent article, the domed section includes part of the top sheet and a cushion section disposed between the top sheet and the absorbent body, the domed section has a center section and an outer peripheral section surrounding the center section, and the density of the cushion section at the outer peripheral section is higher than the density of the cushion section at the center section.

[J2]

The absorbent article according to J1, wherein the absorbent article has a compressed section formed by compressing at least the top sheet and the absorbent body, near the outer edge of the cushion section.

[J3]

The absorbent article according to J1 or J2, wherein the cushion section comprises a plurality of fibers, the intersections between the plurality of fibers being heat-fused.

[J4]

The absorbent article according to any one of J1 to J3, wherein the maximum thickness of the cushion section is 3 to 30 mm.

[J5]

The absorbent article according to any one of J1 to J4, wherein the cushion section retains at least 50% of its maximum thickness after absorption of 2 g of horse EDTA blood, as compared to before horse EDTA blood absorption.

[J6]

The absorbent article according to any one of J1 to J5, wherein the absorbent article has a curved structure in which the domed section curves inward.

[J7]

The absorbent article according to any one of J1 to J6, wherein the absorbent article has an elastic member at both lateral edges in the lengthwise direction.

[J8]

The absorbent article according to any one of J1 to J7, wherein the top sheet has, on the skin contact surface, a plurality of ridges and a plurality of furrows, extending in the lengthwise direction of the absorbent article.

[J9]

The absorbent article according to any one of J1 to J8, wherein the domed section further comprises a blood modifying agent with an IOB of 0-0.60, a melting point of no higher than 45° C. and a water solubility of no greater than 0.05 g in 100 g of water at 25° C.

[J10]

The absorbent article according to J9, wherein the blood modifying agent is (i) a hydrocarbon, (ii) a compound having at least one carbonyl bond (—CO—) and/or at least one ether bond (—O—) inserted between a C—C single bond of a hydrocarbon, or (iii) a compound having at least one carbonyl bond (—CO—) and/or at least one ether bond (—O—) inserted between a C—C single bond of a hydrocarbon, and having at least one hydrogen on the hydrocarbon substituted with a carboxyl group (—COOH) or hydroxyl group (—OH), with the proviso that when 2 or more ether bonds are inserted in a compound of (ii) or (iii), the ether bonds are not adjacent.

[J11]

The absorbent article according to J9 or J10, wherein the blood modifying agent is (i') a hydrocarbon, (ii') a compound having at least one carbonyl bond (—CO—), at least one ester bond (—COO—), at least one carbonate bond (—OCOO—) and/or at least one ether bond (—O—) inserted between a C—C single bond of a hydrocarbon, or (iii') a compound having at least one carbonyl bond (—CO—), at least one ester bond (—COO—), at least one carbonate bond (—OCOO—) and/or at least one ether bond (—O—) inserted between a C—C single bond of a hydrocarbon, and having at least one hydrogen on the hydrocarbon substituted with a carboxyl group (—COOH) or hydroxyl group (—OH), with the proviso that when 2 or more bonds are inserted in a compound of (ii') or (iii'), the bonds are not adjacent.

[J12]

The absorbent article according to any one of J9 to J11, wherein the blood modifying agent is (A) an ester of a compound with 2-4 hydroxyl groups and a compound with 1 carboxyl group, (B) an ether of a compound with 2-4 hydroxyl groups and a compound with 1 hydroxyl group, (C) an ester of a compound with 2-4 carboxyl groups and a compound with 1 hydroxyl group, (D) a compound having one selected from the group consisting of ether bonds (—O—), carbonyl bonds (—CO—), ester bonds (—COO—) and carbonate bonds (—OCOO—) inserted in a hydrocarbon, (E) a poly $C_{2-6}$ alkylene glycol, or its ester or ether, or (F) a chain hydrocarbon.

[J13]

The absorbent article according to any one of J9 to J12, wherein the blood modifying agent is selected from the group consisting of ($A_1$) esters of chain hydrocarbon tetraols and fatty acids, ($A_2$) esters of chain hydrocarbon triols and fatty acids, ($A_3$) esters of chain hydrocarbon diols and fatty acids, ($B_1$) ethers of chain hydrocarbon tetraols and aliphatic monohydric alcohols, ($B_2$) ethers of chain hydrocarbon triols and aliphatic monohydric alcohols, ($B_3$) ethers of chain hydrocarbon diols and aliphatic monohydric alcohols, ($C_1$) esters of chain hydrocarbon tetracarboxylic acids, hydroxy acids, alkoxy acids or oxoacids with 4 carboxyl groups, and aliphatic monohydric alcohols, ($C_2$) esters of chain hydrocarbon tricarboxylic acids, hydroxy acids, alkoxy acids or oxoacids with 3 carboxyl groups, and aliphatic monohydric alcohols, ($C_3$) esters of chain hydrocarbon dicarboxylic acids, hydroxy acids, alkoxy acids or oxoacids with 2 carboxyl groups, and aliphatic monohydric alcohols, ($D_1$) ethers of aliphatic monohydric alcohols and aliphatic monohydric alcohols, ($D_2$) dialkyl ketones, ($D_3$) esters of fatty acids and aliphatic monohydric alcohols, ($D_4$) dialkyl carbonates, ($E_1$) poly $C_{2-6}$ alkylene glycols, ($E_2$) esters of poly $C_{2-6}$ alkylene glycols and fatty acids, ($E_3$) ethers of poly $C_{2-6}$ alkylene glycols and aliphatic monohydric alcohols, ($E_4$) esters of poly $C_{2-6}$ alkylene glycols and chain hydrocarbon tetracarboxylic acids, chain hydrocarbon tricarboxylic acids or chain hydrocarbon dicarboxylic acids, ($E_5$) ethers of poly $C_{2-6}$ alkylene glycols and chain hydrocarbon tetraols, chain hydrocarbon triols or chain hydrocarbon diols, and ($F_1$) chain alkanes.

[J14]

The absorbent article according to any one of J1 to J13, wherein the absorbent article is a sanitary napkin or panty liner.

[J15]

A method for producing an absorbent article according to J2, comprising the steps of:

layering the absorbent body, the cushion section and the top sheet in that order, forming a compressed section near the outer edge of the cushion section by compressing at least the top sheet and the absorbent body, and layering the back sheet on the absorbent body.

REFERENCES SIGNS LIST

1 Absorbent article
2 Domed section
3 Perimeter section
4 Compressed section
5 Top sheet
6 Detaching portion
7 Cushion section
8 Absorbent body
9 Back sheet
10 Anchoring part
11 Center section
12 Outer peripheral section
13 Elastic member

The invention claimed is:

1. An absorbent article comprising a liquid-permeable top sheet, a liquid-impermeable back sheet and an absorbent body between the liquid-permeable top sheet and liquid-impermeable back sheet, wherein the absorbent article has in an excretory opening contact region a domed section that protrudes in the thickness direction of the absorbent article, the domed section includes part of the top sheet and a cushion section disposed between the top sheet and the absorbent body, the domed section has a center section and an outer peripheral section placed at an outer peripheral in a planar direction of the center section so as to surround the center section, and the density of the cushion section at the outer peripheral section is higher than the density of the cushion section at the center section, wherein the domed section is coated with a coating consisting essentially of a blood modifying agent with an Inorganic Organic Balance (IOB) of 0-0.60, a melting point of no higher than 45° C. and a water solubility of no greater than 0.05 g in 100 g of water at 25° C., wherein the coating is configured to infiltrate between blood cells of menstrual blood.

2. The absorbent article according to claim 1, wherein the absorbent article has a compressed section formed by compressing at least the top sheet and the absorbent body, near the outer edge of the cushion section.

3. The absorbent article according to claim 1, wherein the cushion section comprises a plurality of fibers, the intersections between the plurality of fibers being heat-fused.

4. The absorbent article according to claim 1, wherein the maximum thickness of the cushion section is 3 to 30 mm.

5. The absorbent article according to claim 1, wherein the cushion section retains at least 50% of its maximum thickness after absorption of 2 g of horse EDTA blood, as compared to before horse EDTA blood absorption.

6. The absorbent article according to claim 1, wherein the absorbent article has a curved structure in which the domed section curves inward.

7. The absorbent article according to claim 1, wherein the absorbent article has an elastic member at both lateral edges in the lengthwise direction.

8. The absorbent article according to claim 1, wherein the top sheet has, on the skin contact surface, a plurality of ridges and a plurality of furrows, extending in the lengthwise direction of the absorbent article.

9. The absorbent article according to claim 1, wherein the blood modifying agent is
(i) a hydrocarbon,
(ii) a compound having at least one carbonyl bond (—CO—) and/or at least one ether bond (—O—) inserted between a C—C single bond of a hydrocarbon, or
(iii) a compound having at least one carbonyl bond (—CO—) and/or at least one ether bond (—O—) inserted between a C—C single bond of a hydrocarbon, and having at least one hydrogen on the hydrocarbon substituted with a carboxyl group (—COOH) or hydroxyl group (—OH), with the proviso that when 2 or more ether bonds are inserted in a compound of (ii) or (iii), the ether bonds are not adjacent.

10. The absorbent article according to claim 1, wherein the blood modifying agent is
(i') a hydrocarbon,
(ii') a compound having at least one carbonyl bond (—CO—), at least one ester bond (—COO—), at least one carbonate bond (—OCOO—) and/or at least one ether bond (—O—) inserted between a C—C single bond of a hydrocarbon, or
(iii') a compound having at least one carbonyl bond (—CO—), at least one ester bond (—COO—), at least one carbonate bond (—OCOO—) and/or at least one ether bond (—O—) inserted between a C—C single bond of a hydrocarbon, and having at least one hydrogen on the hydrocarbon substituted with a carboxyl group (—COOH) or hydroxyl group (—OH),
with the proviso that when 2 or more bonds are inserted in a compound of (ii') or (iii'), the bonds are not adjacent.

11. The absorbent article according to claim 1, wherein the blood modifying agent is (A) an ester of a compound with 2-4 hydroxyl groups and a compound with 1 carboxyl group, (B) an ether of a compound with 2-4 hydroxyl groups and a compound with 1 hydroxyl group, (C) an ester of a compound with 2-4 carboxyl groups and a compound with 1 hydroxyl group, (D) a compound having one selected from the group consisting of ether bonds (—O—), carbonyl bonds (—CO—), ester bonds (—COO—) and carbonate bonds (—OCOO—) inserted in a hydrocarbon, (E) a poly C2-6 alkylene glycol, or its ester or ether, or (F) a chain hydrocarbon.

12. The absorbent article according to claim 1, wherein the blood modifying agent is selected from the group consisting of (A1) esters of chain hydrocarbon tetraols and fatty acids, (A2) esters of chain hydrocarbon triols and fatty acids, (A3) esters of chain hydrocarbon diols and fatty acids, (B1) ethers of chain hydrocarbon tetraols and aliphatic monohydric alcohols, (B2) ethers of chain hydrocarbon triols and aliphatic monohydric alcohols, (B3) ethers of chain hydrocarbon diols and aliphatic monohydric alcohols, (C1) esters of chain hydrocarbon tetracarboxylic acids, hydroxy acids, alkoxy acids or oxoacids with 4 carboxyl groups, and aliphatic monohydric alcohols, (C2) esters of chain hydrocarbon tricarboxylic acids, hydroxy acids, alkoxy acids or oxoacids with 3 carboxyl groups, and aliphatic monohydric alcohols, (C3) esters of chain hydrocarbon dicarboxylic acids, hydroxy acids, alkoxy acids or oxoacids with 2 carboxyl groups, and aliphatic monohydric alcohols, (D1) ethers of aliphatic monohydric alcohols and aliphatic monohydric alcohols, (D2) dialkyl ketones, (D3) esters of fatty acids and aliphatic monohydric alcohols, (D4) dialkyl carbonates, (E1) poly C2-6 alkylene glycols, (E2) esters of poly C2-6 alkylene glycols and fatty acids, (E3) ethers of poly C2-6 alkylene glycols and aliphatic monohydric alcohols, (E4) esters of poly C2-6 alkylene glycols and chain hydrocarbon tetracarboxylic acids, chain hydrocarbon tricarboxylic acids or chain hydrocarbon dicarboxylic acids, (E5) ethers of poly C2-6 alkylene glycols and chain hydrocarbon tetraols, chain hydrocarbon triols or chain hydrocarbon diols, and (F1) chain alkanes.

13. A method for producing an absorbent article according to claim 2, comprising the steps of:
layering the absorbent body, the cushion section and the top sheet in that order,
forming a compressed section near the outer edge of the cushion section by compressing the top sheet directly onto the absorbent body, and
layering the back sheet on the absorbent body.

14. The absorbent article according to claim 1, wherein the domed section is provided only in the excretory opening contact region.

15. The absorbent article according to claim 1, wherein a projected form in a thickness direction of the domed section is one of roughly circular, roughly elliptical, roughly rounded rectangular, or a figure surrounded by two arcs.

16. The absorbent article according to claim 1, wherein a density of the cushion section ranges from 0.001 to 0.1 g/cm$^3$.

17. The absorbent article according to claim 1, wherein a density of the cushion section at the outer peripheral section of the domed section is 1.1 to 5.0 times higher than a density of the cushion section at the center section of the domed section.

18. The absorbent article according to claim 1, wherein the cushion section has a length of 50 to 100 mm in a lengthwise direction and a length of 25 to 50 in a widthwise direction.

19. The absorbent article according to claim 1, wherein the coating is configured to prevent formation of rouleau structures by the blood cells of menstrual blood.

20. An absorbent article comprising a liquid-permeable top sheet, a liquid-impermeable back sheet and an absorbent body between the liquid-permeable top sheet and liquid-impermeable back sheet, wherein the absorbent article has in an excretory opening contact region a domed section that protrudes in the thickness direction of the absorbent article, the domed section includes part of the top sheet and a cushion section disposed between the top sheet and the absorbent body, the domed section has a center section and an outer peripheral section placed at an outer peripheral in a planar direction of the center section so as to surround the center section, and the density of the cushion section at the outer peripheral section is higher than the density of the cushion section at the center section, wherein the domed section is coated with a coating consisting essentially of a blood modifying agent with an Inorganic Organic Balance (IOB) of 0-0.60, a melting point of no higher than 45° C. and a water solubility of no greater than 0.05 g in 100 g of water at 25° C., the coating has an affinity with menstrual blood, and the coating is configured to migrate from the top sheet to the absorbent body with the menstrual blood.

* * * * *